United States Patent [19]
Matsushita

[11] Patent Number: 5,973,776
[45] Date of Patent: Oct. 26, 1999

[54] SURFACE INSPECTION APPARATUS

[75] Inventor: Hidekatsu Matsushita, Kyoto, Japan

[73] Assignee: Matsushita Seiki Co., Ltd., Kyoto, Japan

[21] Appl. No.: 09/059,426

[22] Filed: Apr. 13, 1998

[30] Foreign Application Priority Data

| Apr. 15, 1997 | [JP] | Japan | 9-097208 |
| Sep. 3, 1997 | [JP] | Japan | 9-238590 |
| Nov. 12, 1997 | [JP] | Japan | 9-310310 |

[51] Int. Cl.[6] ................................. G01N 21/00
[52] U.S. Cl. ................. 356/237.4; 356/400; 355/53
[58] Field of Search ............ 356/237.1, 237.2, 356/237.3, 237.4, 237.5, 399–401, 394; 250/548; 355/53, 54, 55

[56] References Cited

U.S. PATENT DOCUMENTS

| 4,902,900 | 2/1990 | Kamiya et al. | 356/400 |
| 5,066,131 | 11/1991 | Iwata et al. | 356/401 |
| 5,461,237 | 10/1995 | Wakamoto et al. | 356/401 |
| 5,717,482 | 2/1998 | Akutsu et al. | 356/400 |
| 5,737,063 | 4/1998 | Miyachi | 356/400 |
| 5,831,739 | 11/1998 | Ota | 356/401 |
| 5,850,291 | 12/1998 | Tsutsui | 356/401 |

*Primary Examiner*—Hoa Q. Pham
*Attorney, Agent, or Firm*—Merchant & Gould P.C.

[57] ABSTRACT

A device enabling an inspector to inspect a surface of a photomask etc. without holding the photomask manually, and enabling him/her not to lose his/her sight of any defect of the surface even if the surface is tilted. The device includes a hemispherical support, with its open side upward, which is supported so as to slidably move along a spherical surface with a point S as its center, an X-Y stage which is fixed onto the hemispherical support, a rotation unit which is mounted onto the X-Y stage, a support plate which is supported onto the rotation unit, a lighting device which lights up a part of a photomask, on the support plate, corresponding to the spot S and its vicinity. The support plate can be tilted about the spot S.

9 Claims, 11 Drawing Sheets

SURFACE INSPECTION APPARATUS

BACKGROUND OF THE INVENTION

1. Field of the Invention

The present invention relates to a surface inspection apparatus for inspecting a surface of a photomask or the like, and particularly relates to the surface inspection apparatus for inspecting whether or not there is a particle of dust and/or a flaw on the surface of the photomask or the like.

2. Description of the Related Arts

Generally, if there is a particle of dust or a flaw on a mask surface of a photomask which is used for exposing a semiconductor wafer to a light so as to correspond to a circuit pattern, the particle of dust or the flaw is exposed to the light as a part of the circuit pattern. As a result, a wafer with a defect is produced. Accordingly, it is crucially important to prevent the particle of dust or the flaw from being deposited or formed on the photomask.

In order to prevent the dust or flaw from being on the photomask, a visual final inspection thereof has been performed conventionally. The visual final inspection thereof is carried out after an inspection with an automatic inspection apparatus is done, as a conventional common practice. The reason why the visual final inspection is carried out is that the automatic inspection apparatus has a stationary camera which is used for scanning the mask surface only level or in a direction generally perpendicular to the surface thereof. That is, the mask surface thereof can not be inspected in different directions with the stationary camera; therefore, there is a possibility that the stationary camera may overlook the particle of dust or the flaw thereon. This visual final inspection has been conventionally carried out completely manually.

More specifically, at the step of the visual final inspection, an inspector inspects the photomask in such a manner that he/she visually observes the mask surface under a lighting while he/she is changing the angle between the mask surface and the lighting, while manually holding the photomasks one by one. At this step thereof, if there is a particle of dust or a flaw on the mask surface, the defect can be found by observing any specific, irregular reflection caused thereby.

The method is, however, extremely primitive. According to the method, because the inspector directly holds the photomask with his/her own hand, the photomask may be, on the contrary, spoiled by a particle of dust adhered on the mask surface thereof with the inspector's intervention.

Further, when the inspector repeats the inspecting process many times, the inspector's hand is fatigued, and the efficiency of the inspection thereof is significantly lower.

Furthermore, in addition to the visual inspection on the mask surface, it is necessary to do such extra works as fixing the position of the photomask, or inclining the photomask ideally, which also cause an inefficiency in the inspecting work.

In order to solve these problems, it is conceivable that the photomask is handled with a robot, or the like, in a space which is isolated from the inspector, where the photomask is placed onto an inspection stage and the inspector visually inspects the photomask through an observation window. In such system, it is desirable to do a remote control or do an automatic control of the photomask so that the photomask is carried from place to place in the system and is properly handled, and so that the photomask which is placed on the inspection stage is positioned relative to the inspection stage, is moved, and is inclined.

Meanwhile, as to the inspection of the wafer, there has been conventionally provided a surface inspection apparatus which allows the inspector to visually inspect the wafer without directly touching it. This surface inspection apparatus is equipped with a suction disk for sucking the wafer which is placed on top of the suction disk, in which the suction disk is inclinable generally in a circular arc about pivot located in lower part of the apparatus. The inspector, while inclining the wafer by operating a joy stick, performs a visual inspection under an illumination of a spotlight, or a lighting.

However, according to this surface inspection apparatus, when the wafer is intentionally inclined for a review of observation, detailed investigation, and/or checking of a defect of the wafer from a different angle, upon a discovery of the defect thereof, the defect moves together with the wafer due to the inclination of the wafer. Accordingly, with the surface inspection apparatus, there arises a problem that the inspector is prone to lose sight of the defect of the wafer.

Particularly, when the spotlight is made to be smaller at the time of the inspector's trying to do a more precise inspection of the wafer, only a small part of the wafer surface is illuminated or lit by the spotlight with the inspection range being narrower. At this time, the defect of the wafer immediately goes out of the inspection range if the inspector tilts or inclines the wafer.

Meanwhile, it is desirable that this type of surface inspection apparatus is as compact as possible.

SUMMARY OF THE INVENTION

Therefore, one object of the present invention is to provide a surface inspection apparatus for inspecting the surface of a planar body as an object to be inspected such as the photomask or the like, by which it is possible to inspect the surface of the planar body without holding the planar body by a man's hand and by which the sight of the defect on the surface of the planar body is not lost even if the planar body is tilted or inclined.

Another object of the present invention is to provide the surface inspection apparatus which can be as miniaturized as possible.

In accomplishing these and other objects of the present invention, the present invention has a fundamental characterization that a surface to be inspected of a planar object is tilted or rotated about a stationary point which is illuminated or lit by a spotlight.

More specifically, according to one aspect of the present invention, there is provided a surface inspection apparatus comprising: a support plate on which a planar object, such as a photomask, to be inspected is put; a lighting device which lights a point (also, hereinafter, referred to as "a spot") and a vicinity of the point of a surface to be inspected of the planar object that is put on the support plate; a first driving device which is supported by a stationary base, and which tilts or rotates the support plate about a tilting point corresponding to the point, i.e. the spot, of the surface lit up by the lighting device so that a normal line to the surface, i.e. a line perpendicular to the surface, passing the tilting point, of the planar object tilts or inclines in every direction; and a second driving device which moves the support plate in two directions, generally perpendicular to each other, along the surface of the planar object which is put on the support plate.

According to the mechanism, the planar object is put on the support plate, and the surface to be inspected of the planar object is illuminated or lit by the lighting device. The spot lit by the lighting device is stationary and fixed. The second driving device moves the support plate in two directions along the surface of the planar object which is put on the support plate in a specified pattern so that the surface of the planar object is moved relative to the stationary spot. With this movement of the surface of the planar object relative to the stationary base, the spot moves on the surface of the planar object sequentially in accordance with the specified pattern so that the spot and its vicinity of the spot cover all the surface of the planar object.

When the inspector discovers or finds any defect, such as a debris, a particle of dust or a flaw, on the surface of the planar object at a region corresponding to the spot or its vicinity, he/she can actuate the first driving device so as to properly tilt or incline the surface to be inspected of the planar object in order to change a lighting angle of the lighting device relative to the surface to be inspected thereof. With the actuation of the first driving device, the inspector can inspect the defect in detail.

In this operation of the first driving device, the surface to be inspected of the planar object tilts or inclines about the spot. Therefore, the defect thus found within the illuminating region remains within the same during the operation of the first driving device.

Therefore, according to the mechanism, it is realized not only that the inspection of the surface thereof can be carried out with the planar object being held without using the inspector's manual hold, but also that the inspector does not lose sight of the defect even if he/she tilts the planar object.

Preferably, there is further provided a third driving device which rotates the support plate about a rotation axis which is parallel to the normal line to the surface of the planar object which is put on the support plate.

According to this mechanism, it is possible to inspect the planar object while changing the orientation of the planar object, by rotating the planar object by the third driving device. Namely, with the mechanism, it is possible to enhance the accuracy of the inspection thereof.

Preferably, there is further provided a bowl-like support generally hemispherical in shape that has a peripheral surface corresponding to a part of a sphere with a center point corresponding to the point lit up by the lighting device of the planar object, wherein the support plate is provided inside the bowl-like support in which the planar object is supported on the support plate so that the planar object is positioned at a level which is generally equal to a level of a periphery of the bowl-like support, wherein the second driving device is provided inside the bowl-like support, and wherein the first driving device moves the bowl-like support along the sphere.

According to the mechanism, the peripheral surface, or the outer surface, of the bowl-like support is a sphere. Therefore, when the first driving device drives to move the bowl-like support along the sphere, a center of the sphere does not move. Namely, the bowl-like support tilts or inclines about a center point which corresponds to the center of the sphere.

Also, according to the mechanism, the planar object is held by the support plate at the level which is generally equal to the level of the periphery of the bowl-like support. Therefore, within a region of inclination of the bowl-like support, it is easy to construct the surface inspection apparatus so that the inspector's eye(s) (line of sight or line of view) is/are not prevented from reaching the surface to be inspected of the planar object by the bowl-like support, and/or so that a light emitted from the lighting device is not prevented from reaching the surface thereof thereby. That is, the planar object can be inclined or tilted about the spot with a simple construction.

Preferably, there is further provided a third driving device which rotates the support plate about a rotation axis which is parallel to the normal line to the surface of the planar object which is put on the support plate.

According to this mechanism, it is possible to inspect the planar object while changing the orientation of the planar object by rotating the planar object by the third driving device. Namely, with the mechanism, it is possible to enhance the accuracy of the inspection thereof.

Preferably, the first driving device comprises a supporting member which supports the bowl-like support, a pair of drive belts, and a belt drive device. The supporting member slidably or movably supports the bowl-like support along the periphery thereof. The pair of drive belts are provided generally along the periphery thereof so that the pair of drive belts cross generally perpendicular to each other. Both ends of the drive belt are connected on a periphery of the bowl-like support at locations opposite to each other relative to the tilting point. The belt drive device moves each of the drive belts generally in a direction in which each thereof extends.

According to the mechanism, when the belt drive device pulls the drive belt, the bowl-like support tilts or inclines in a direction in which the drive belt is pulled. The inclination of the bowl-like support in the two directions perpendicular to each other driven by the movements of the two drive belts, enables the support plate to be tilted or inclined so that the normal line, passing the tilting point, to the surface to be inspected of the planar object can tilt or incline in every direction. Namely, the first driving device can be simple in construction.

Alternatively, the first driving device may comprise: at least three longitudinal links which are provided around a standard axis that passes the tilting point and that is generally perpendicular to the surface of the planar object, and which are provided generally parallel to the standard axis, in which each of the at least three longitudinal links is connected to one of the support plate and a plate support member that supports the support plate; and a rising and falling device for making the longitudinal link rise and fall along the standard axis, wherein at least one of the longitudinal links and the standard axis form a first link pair, wherein there is provided a second link pair which is provided parallel to the surface of the planar object, in which the first link pair and the second link pair form a parallel link mechanism, and wherein the at least one of the longitudinal links, and one of the support plate and the plane support member, are prevented from rotating relative to each other about an axis which corresponds to a direction in which the at least one of the longitudinal links extends.

According to this mechanism, the at least one of the longitudinal links, and one of the support plate and the plane support member, are prevented from rotating relative to each other about the axis which corresponds to the direction in which the at least one of the longitudinal links extends. Therefore, when the at least one of the longitudinal links is made to go up and down, namely when the other(s) of the longitudinal links is/are made to go up and down, by actuating the rising and falling device, the surface to be inspected of the planar object is tilted or inclined so that the tilting point, namely, the spot on the surface to be inspected the planar object, remains stationary.

For instance, as a simple example, the surface inspection apparatus may be constructed as follows: three longitudinal links are provided every 120° around the tilting point; and a connecting point which connects one of the three longitudinal links to one of the support plate and the plate support member, is aligned on a straight line on which a pair of connecting points which connect the parallel link mechanism to the one of the three longitudinal links. With the mechanism, when the one of the three longitudinal links goes up and down, the tilting point i.e. the spot on the surface to be inspected of the planar object moves within a plane including each link of the parallel link mechanism. At this time, even if the tilting point i.e. the spot on the surface to be inspected of the planar object moves away from the standard axis, it is possible to return the tilting point i.e. the spot on the surface thereof back to its original position on the standard axis by making the other two longitudinal links go up and down properly. Accordingly, the support plate, the plate support member, or the surface to be inspected of the planar object, can be rotated i.e. tilted about a line perpendicular to a plane which passes the tilting point and includes each link of the parallel link mechanism.

By making the other longitudinal links go up and down with the tilting point being positioned on the standard axis, the support plate or the plate support member or the surface to be inspected of the planar object can be rotated i.e. tilted about a straight line which passes both the tilting point and a connecting point between at least one of the longitudinal links and one of the support plate and the plate support member.

According to the mechanism, it is possible to rotate i.e. tilt or incline the surface to be inspected of the planar object about the tilting point in every direction by making at least three longitudinal links go up and down in a proper way with the rising and falling device.

Therefore, according to the mechanism, it is realized not only that the inspection of the surface thereof can be carried out with the planar object being held without using the inspector's manual hold, but also that the inspector does not lose sight of the defect even if he/she tilts the planar object.

Also, according to the mechanism, it is possible to provide each longitudinal link near the support plate or the plate support member. Consequently, the miniaturization of the apparatus can be facilitated.

Preferably, the first driving device comprises a parallel link drive mechanism and a link ascending and descending mechanism, wherein the parallel link drive mechanism comprises: a pair of first lateral links which are provided parallel to the surface of the planar object within a standard plane which includes a standard axis that passes the tilting point and is generally perpendicular to the surface of the planar object, in which a middle part of each of the pair of first lateral links is rotatably mounted to the stationary base via a rotation axis that passes the standard axis and is perpendicular to the standard plane; and a pair of first longitudinal links which are provided on both sides of the standard axis within the standard plane so as to be parallel to the standard axis, in which the pair of first longitudinal links are rotatably connected to both ends of each of the pair of first lateral links, and in which the pair of first longitudinal links are rotatably connected to one of the support plate and a plate support member that supports the support plate, through at least a first joint, within the standard plane, wherein the link ascending and descending mechanism comprises: a second lateral link which is provided parallel to the surface of the planar object within a plane that passes the standard axis and is perpendicular to the standard plane, in which one of the ends of the second lateral link is mounted on the stationary base rotatably about a rotation axis which is perpendicular to the standard axis within the standard plane; and a second longitudinal link which is provided generally parallel to the standard axis in a region including the plane that passes the standard axis and is perpendicular to the standard plane, in which one of the ends of the second longitudinal link is rotatably connected to the other of the ends of the second lateral link through a second joint, and in which the other of the ends of the second longitudinal link is rotatably connected to one of the support plate and the plate support member through a third joint.

In the mechanism, when the parallel link mechanism is actuated, the first lateral link is rotated about the middle part within the standard plane so that one end of the first lateral link goes up and the other end thereof goes down. The pair of first lateral links are provided so that they are parallel to each other. Therefore, a line which connects both connecting points between the support plate and the pair of first longitudinal links, or a line which connects both connecting points between the plate support member and the pair of first longitudinal links, rotates or tilts about an intersection between the line and the standard axis, namely about the tilting point, within the standard plane. That is, the surface to be inspected of the planar object is rotated or tilted about a line which passes the tilting point and is perpendicular to the standard plane.

On the other hand, when the link ascending and descending mechanism is actuated, the second lateral link is rotated or tilted about one end point thereof within a plane which passes the standard axis and is perpendicular to the standard plane, so that the second longitudinal link is made to go up and down. Accompanying this movement of the second longitudinal link, a connecting point between the second longitudinal link, and one of the support plate and the plate support member is made to go up and down. That is, the surface to be inspected of the planar object is rotated or tilted about a line which connects both connecting points between the support plate and the pair of first longitudinal links of the parallel link drive mechanism, or is rotated or tilted about a line which connects both connecting points between the plate support member and the pair of first longitudinal links thereof.

According to the mechanism, a rotation or inclination of the surface to be inspected of the planar object on the support plate or the plate support member driven by the parallel link drive mechanism and a rotation or inclination of the surface to be inspected of the planar object on the support plate or the plate support member driven by the link ascending and descending mechanism, are combined to each other so that the surface to be inspected of the planar object thereon can be rotated or inclined in every direction.

Also, according to the mechanism, it is possible to facilitate a miniaturization of the apparatus, to make the apparatus simple in construction, and to facilitate a control for tilting or inclining the surface to be inspected of the planar object.

In the mechanism, the first joint may comprise a joint body in which the one of the support plate and the plate support member can rotate relative to the joint body about an axis that is perpendicular to the standard axis within the standard plane, and in which the first longitudinal link can rotate relative to the joint body about an axis that is perpendicular both to the standard axis and to the standard plane, wherein the second joint may be a universal joint, and wherein the third joint may comprise a joint body in which the one of the support plate and the plate support member can rotate relative to the joint body of the third joint about an axis that is perpendicular both to the standard axis and to the standard plane, and in which the second longitudinal link can rotate relative to the joint body of the third joint about an axis that is parallel to the standard plane and that is perpendicular to the standard axis.

More specifically, for example, the first joint may comprise: a pin which extends from an end of the one of the support plate and the plate support member in which the pin extends in a direction of the axis that is perpendicular to the standard axis and that is parallel to the standard plane; a hole which forms on the joint body of the first joint in which the pin of the first joint rotatably engages the hole; a pin which extends from an end of the first longitudinal link in which the pin extends in the direction that is perpendicular both to the standard plane and to the standard axis; and a hole which forms on the joint body of the first joint in which the pin of the first longitudinal link rotatably engages the hole, wherein the universal joint may be a ball joint, and wherein the third joint may comprise: a pin which extends from an end of the one of the support plate and the plate support member in which the pin extends in a direction that is perpendicular both to the standard axis and to the standard plane; a hole which forms on the joint body of the third joint in which the pin of the one of the support plate and the plate support member rotatably engages the hole of the third joint; a pin which extends from an end of the second longitudinal link in which the pin extends in the direction that is parallel to the standard plane and that is perpendicular to the standard axis; and a hole which forms on the joint body of the third joint in which the pin of the second longitudinal link rotatably engages the hole.

Alternatively, the first driving device may comprise a parallel link drive mechanism and a link ascending and descending mechanism, wherein the parallel link drive mechanism comprises: a first lateral link which is provided parallel to the surface of the planar object within a standard plane which includes a standard axis that passes the tilting point and that is generally perpendicular to the surface of the planar object, in which a middle part of the first lateral link is rotatably mounted to the stationary base via a rotation axis that passes the standard axis and is perpendicular to the standard plane; and a pair of first longitudinal links which are provided generally parallel to the standard axis in a region including the standard plane and which are provided on both sides of the standard axis, in which one of the ends of each first longitudinal link is rotatably connected to each end of the first lateral link through a first joint, and in which the other of the ends of each first longitudinal link is rotatably connected to one of the support plate and a plate support member which supports the support plate, through a second joint, wherein the link ascending and descending mechanism comprises: a pair of second lateral links which are provided parallel to the surface of the planar object within a plane which passes the standard axis and is perpendicular to the standard plane, in which one of the ends of each second lateral link is rotatably supported by the stationary base through a rotation axis that is perpendicular to the standard axis within the standard plane, and in which the other of the ends of one of the second lateral links and the other of the ends of the other of the second lateral links are on a same side relative to the standard axis; and a second longitudinal link which are provided parallel to the standard axis within the plane which passes the standard axis and is perpendicular to the standard plane, in which the second longitudinal link is rotatably connected to the others of the ends of the second lateral links through a pair of axes that are perpendicular to the standard axis and that are parallel to the standard plane, and in which the second longitudinal link is rotatably connected to one of the support plate and the plate support member through a third joint within the plane that is perpendicular to the standard plane with a state in which the second longitudinal link and the one of the support plate and the plate support member are prevented from rotating relative to each other about an axis which corresponds to a direction in which the second longitudinal link extends.

In the mechanism, when the link ascending and descending mechanism is actuated, the pair of second lateral links are made to go up and down, and the second longitudinal link is also made to go up and down. Accompanying this movement of the second longitudinal link, a connecting point between the second longitudinal link, and one of the support plate and the plate support member, is made to go up and down. With the movement of the connecting point, the surface to be inspected of the planar object is rotated or tilted about a line which passes both connecting points between the support plate and the pair of first longitudinal links, or is rotated or tilted about a line which passes both connecting points between the plate support member and the pair of first longitudinal links.

On the other hand, when the parallel link drive mechanism is actuated, the first lateral link is rotated or tilted, so that one of the first longitudinal links is made to go up and the other thereof is made to go down. Accompanying this movement thereof, one connecting point between the support plate or plate support member, and one of the first longitudinal links is made to go up, while the other connecting point between the support plate or plate support member, and the other of the first longitudinal links is made to go down. With this movement of the connecting points therebetween, the surface to be inspected of the planar object is rotated or tilted about a line which passes the tilting point and is perpendicular to the standard plane.

According to the mechanism, a rotation or inclination of the surface to be inspected of the planar object on the support plate or the plate support member driven by the parallel link drive mechanism and a rotation or inclination of the surface to be inspected of the planar object on the support plate or the plate support member driven by the link ascending and descending mechanism are combined to each other so that the surface to be inspected of the planar object thereon can be rotated or inclined in every direction.

Also, according to the mechanism, it is possible to facilitate a miniaturization of the apparatus, to make the apparatus simple in construction, and to facilitate a control for tilting or inclining the surface to be inspected of the planar object.

In the mechanism, the first joint may be a universal joint, wherein the second joint may comprise a joint body in which the one of the support plate and the plate support member can rotate relative to the joint body about an axis that is perpendicular to the standard axis and that is parallel to the standard plane, and in which the first longitudinal link can rotate relative to the joint body about an axis that is perpendicular both to the standard axis and to the standard plane, and wherein the third joint may comprise a joint body in which the one of the support plate and the plate support member can rotate relative to the joint body of the third joint about an axis that is perpendicular both to the standard axis and to the standard plate, and in which the second longitudinal link can rotate relative to the joint body of the third joint about an axis that is perpendicular to the standard axis and that is parallel to the standard plane.

More specifically, the universal joint may be a ball joint, wherein the second joint may comprise a pin which extends from an end of the one of the support plate and the plate support member in which the pin extends in a direction of the axis that is perpendicular to the standard axis and that is parallel to the standard plane; a hole which forms on the joint body of the second joint in which the pin of the second joint rotatably engages the hole; a pin which extends from an end of the first longitudinal link in which the pin extends in the direction that is perpendicular both to the standard plane and to the standard axis; and a hole which forms on the joint body of the second joint in which the pin of the first longitudinal link rotatably engages the hole, and wherein the third joint may comprise: a pin which extends from an end of the one of the support plate and the plate support member in which the pin extends in a direction that is perpendicular both to the standard axis and to the standard plane; a hole which forms on the joint body of the third joint in which the pin of the one of the support plate and the plate support member rotatably engages the hole of the third joint; a pin which extends from an end of the second longitudinal link in which the pin extends in the direction that is parallel to the standard plane and that is perpendicular to the standard axis; and a hole which forms on the joint body of the third joint in which the pin of the second longitudinal link rotatably engages the hole.

BRIEF DESCRIPTION OF THE DRAWINGS

These and other objects and features of the present invention will become clear from the following description taken in conjunction with the preferred embodiments thereof with reference to the accompanying drawings, in which.

DETAILED DESCRIPTION OF THE PREFERRED EMBODIMENTS

Figure 2:
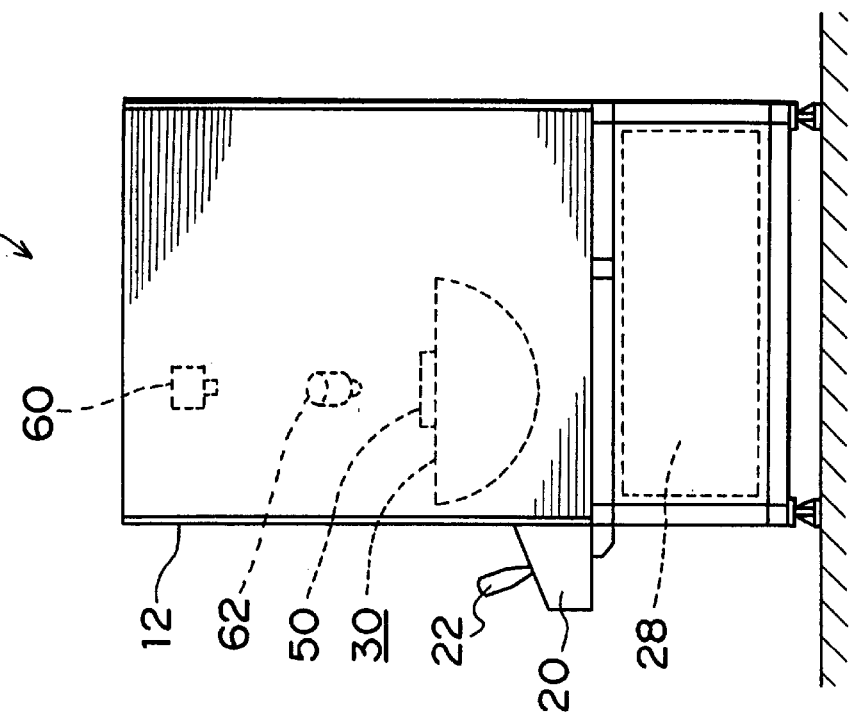
FIG. 2 is a side view of the photomask surface inspection apparatus shown in FIG. 1.

Before the description of the present invention proceeds, it is to be noted that like or corresponding parts are designated by like reference numerals throughout the accompanying drawings.

Referring to FIGS. 1 through 14, a detailed description is made below on a photomask surface inspection apparatus 10, 100, 100x according to each of three embodiments of the present invention.

First, referring to FIGS. 1 through 9, the description is made below on the photomask surface inspection apparatus 10 according to a first embodiment of the present invention.

Figure 1:
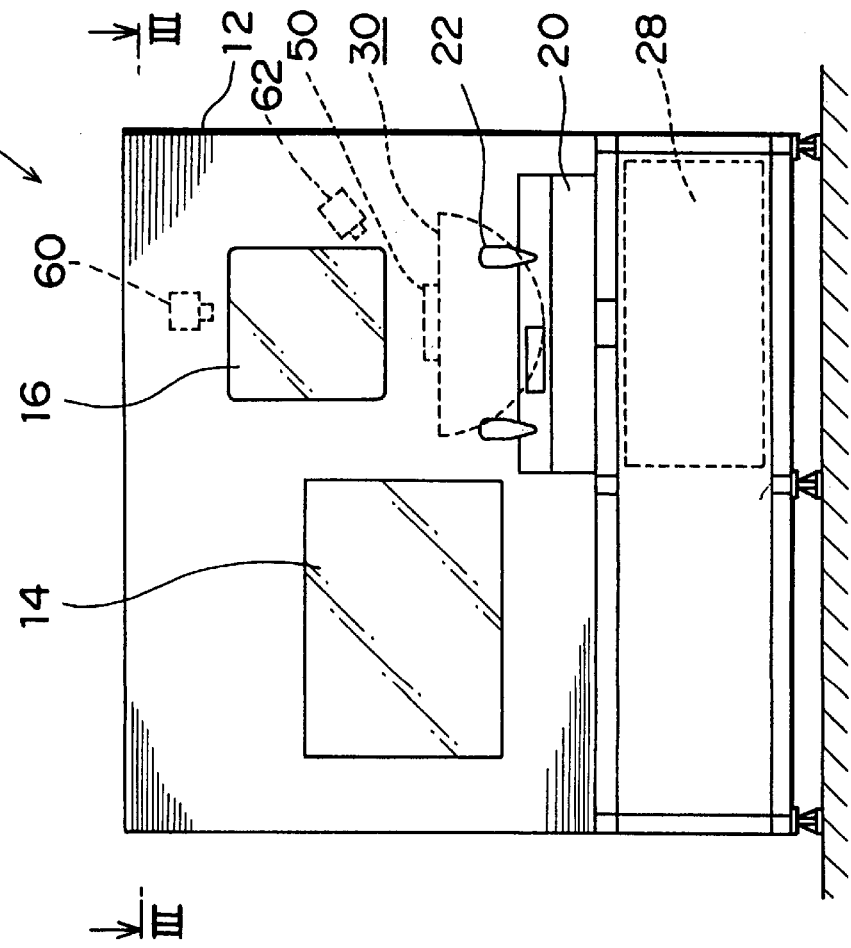
FIG. 1 is a front view of a photomask surface inspection apparatus according to a first embodiment of the present invention.

This photomask surface inspection apparatus 10 generally comprises an apparatus body 12 and an operation unit 20, as shown in a front view of FIG. 1, and as shown in a side view of FIG. 2.

The apparatus body 12 generally comprises, in its interior, an unshown first stage, an unshown second stage, an unshown transfer robot, an inspection stage unit 30, a first illuminating lamp 60, a second illuminating lamp 62, and a control unit 28.

A storage case I for storing a plurality of photomasks which are not yet inspected is installed on the first stage, and a storage case II for storing a plurality of photomasks which are already inspected is installed on the second stage. The transfer robot performs a transfer and handling of the photomask. That is, the transfer robot, for example, takes one piece of photomask out of the storage case I installed on the first stage, puts the photomask on a support plate 50 of the inspection stage unit 30, inverts or overturns the photomask on the support plate 50 of the inspection stage unit 30, and transfers the photomask placed on the support plate 50 thereof to the storage case II on the second stage.

The inspection stage unit 30, which is described in detail later, moves, tilts or rotates the support plate 50 for its surface inspection of the photomask placed on the support plate 50.

The first and second illuminating lamps 60, 62 illuminate the photomask being placed on the support plate 50, from above and from side relative to the photomask, respectively.

The control unit 28 controls the operation of the transfer robot, the inspection stage unit 30, etc.

In the apparatus body 12, there are provided a door 14 through which the storage case I and the storage case II, having the photomask(s) housed therein, are taken in and out, and an inspection window 16 through which an inspector can observe or inspect the photomask placed on the support plate 50 of the inspection stage unit 30 from outside of the apparatus body 12. With the mechanism, the inside of the apparatus body 12 is maintained clean.

On the operation unit 20, there are arranged a pair of joy sticks 22, unshown various control buttons, etc. so that the operation unit 20 can operate the transfer robot, the inspection stage unit 30, etc.

Next, the mechanism of the inspection stage unit 30 is described in more detail with reference to FIGS. 3 to 5.

Figure 3:
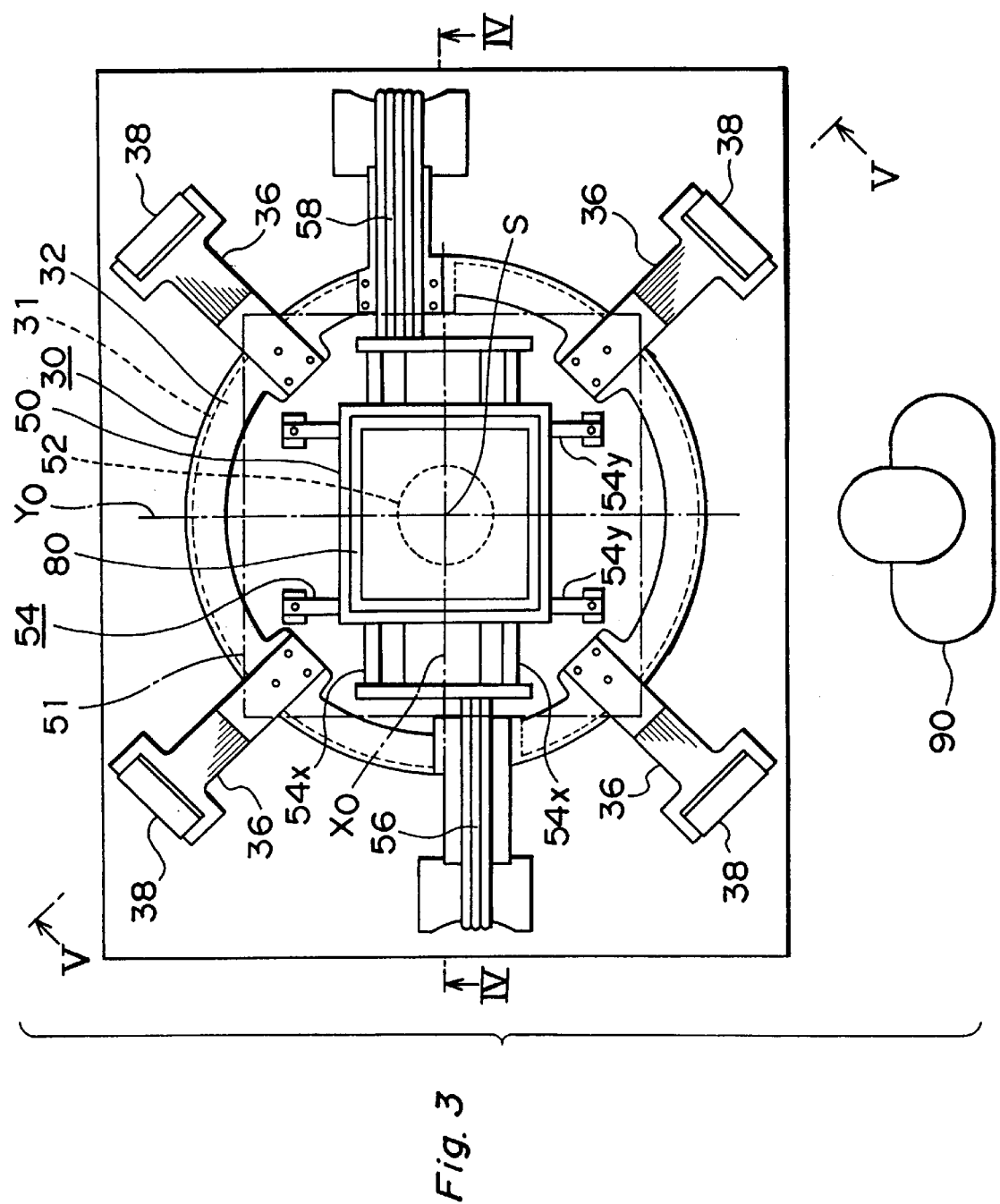
FIG. 3 is a plan view of an inspection stage unit of the photomask surface inspection apparatus of FIG. 1.
Figure 4:
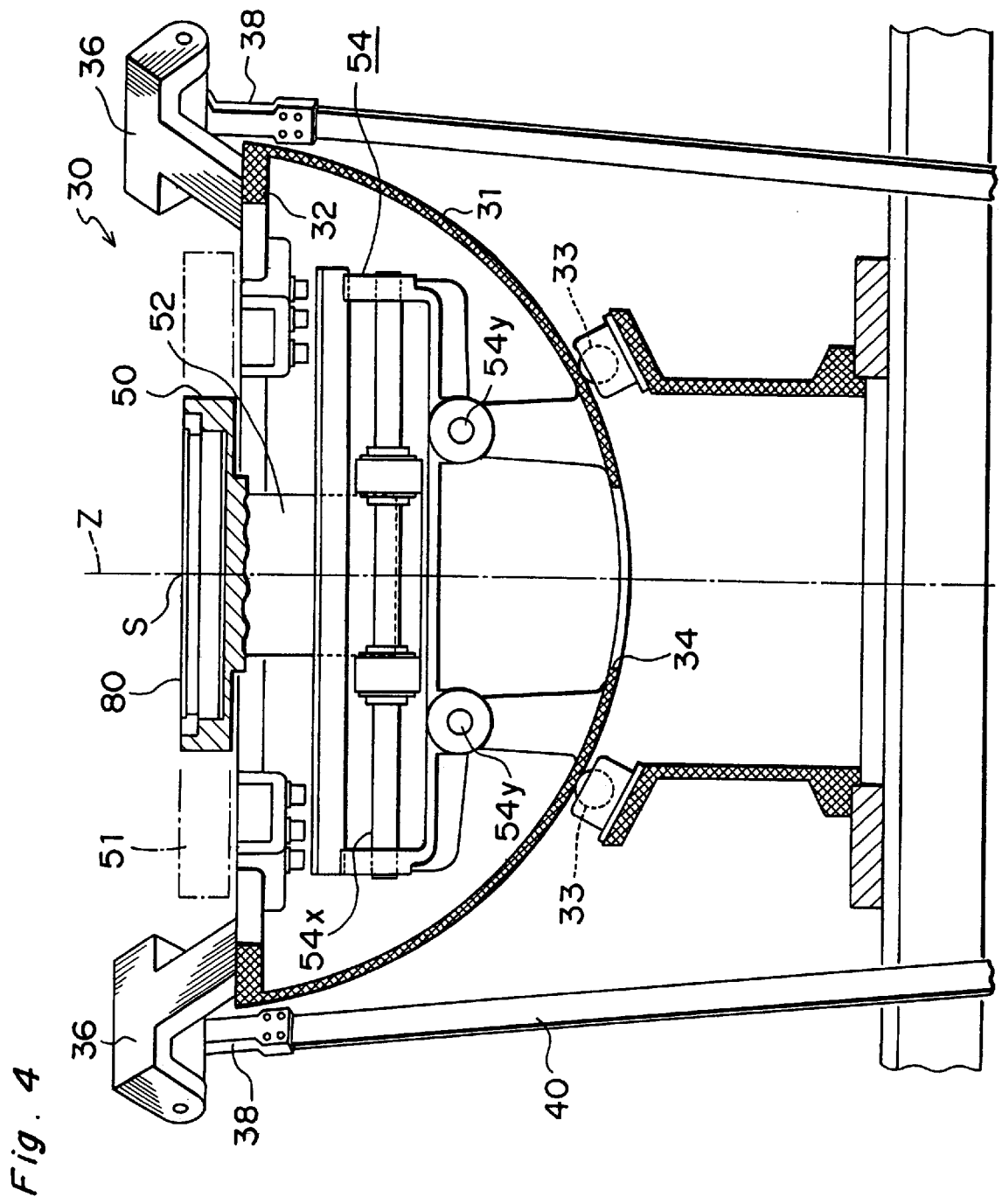
FIG. 4 is a schematic central sectional view taken generally along the line IV—IV of FIG. 3.
Figure 5:
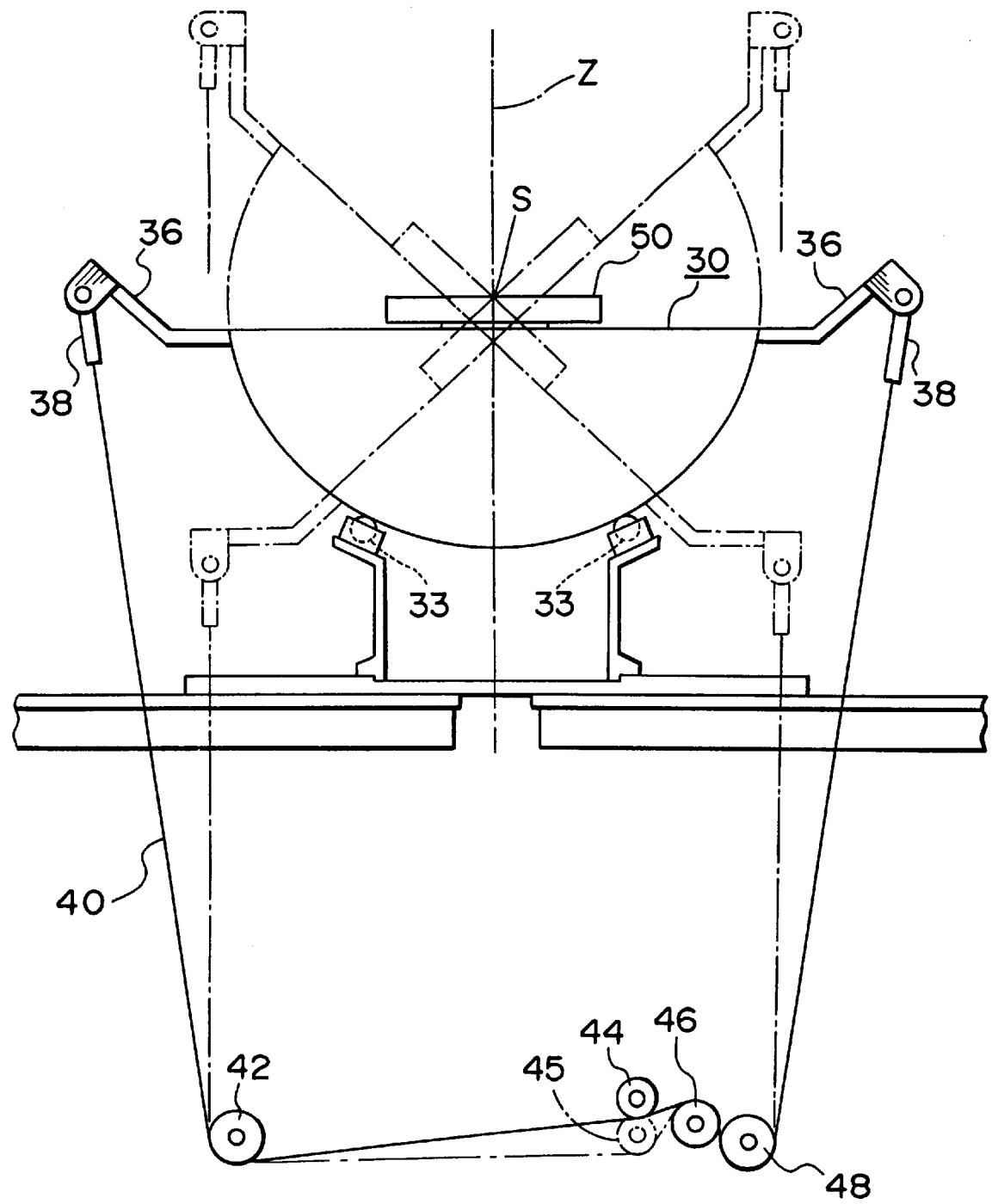
FIG. 5 is a schematic view taken generally along the line V—V of FIG. 3.

FIG. 3 is a plan view of the inspection stage unit 30, FIG. 4 is a schematic central sectional view taken generally along the line IV—IV of FIG. 3, and FIG. 5 is a schematic explanatory view taken generally along the line V—V of FIG. 3.

The inspection stage unit 30 comprises a generally hemispherical support 31 which is disposed with its opening side being directed upward, an X-Y stage 54 which is fixed to the hemispherical support 31, a rotation unit 52 which is movably mounted on the X-Y stage 54, and a support plate 50 which is rotatably fixed on the rotation unit 52.

The X-Y stage 54 which is fixed on the generally hemispherical support 31, comprises a guide shaft 54x, and a guide shaft 54y which extends in a direction perpendicular to the guide shaft 54x. With the pair of guide shafts 54x and 54y, the rotation unit 52 can be guided in two directions of $X_0$ and $Y_0$ so that the support plate 50 can be moved to any desired position within a moving area 51, which is shown by a one-dot chain line.

The rotation unit 52 rotates the support plate 50 about a center of the support plate 50. To the X-Y stage 54 and the rotation unit 52, are connected cables 56, 58 which are used for transmitting an electric power, signals, etc. The cables 56, 58 are disposed so as to pass the periphery of the generally hemispherical support 31.

The generally hemispherical support 31 is provided with an air vent hole 34 for forming an air flow from above to below in order to prevent a deposition of dusts relative to a photomask 80. The generally hemispherical support 31 is supported by ball bearings 33 at its outer peripheral lower part, and is so arranged that the generally hemispherical support 31 can be inclined or tilted as a whole in any desired direction along the outer peripheral surface with a movement of a pair of drive belts 40 for driving the hemispherical support 31 in which one of the drive belts 40 extends perpendicular to the other thereof.

More specifically, the outer peripheral surface of the generally hemispherical support 31 is a part of spherical surface having a center which corresponds to one point, i.e. a spot S, of the photomask 80 placed on the support plate 50 which is in a standard position. There are provided four drive belt mounting arms 36 around a flange 32 of the hemispherical support 31 so that each pair of adjacent drive belt mounting arms 36, 36 form 90° relative to the center of the hemispherical support 31, and so that each drive mounting arm 36 projects upwardly and outwardly. To the end of each drive belt mounting arm 36, a drive belt fitting device 38 is rotatably connected.

The drive belt mounting arms 36 are provided at positions about 45° shifted with respect to the $X_0$- and $Y_0$-directions so as not to interrupt the inspector's sight relative to a photomask 80 put on the support plate 50 when he/she observes the photomask 80 on the support plate 50 through the inspection window 16.

Each drive belt 40 has a plurality of teeth on its outer surface. Both ends of each of the two drive belts 40 are fixed to the drive belt fitting devices 38 which are rotatably connected to the drive belt mounting arms 36. The pairs of drive belt mounting arms 36 to which the pairs of both ends of the two drive belts 40 are connected, are positioned symmetrically relative to a center axis Z of the hemispherical support 31. As illustrated in FIGS. 4 and 5, the pairs of drive belts 40 extend under the hemispherical support 31.

Each drive belt 40 is guided under the lower part of the generally hemispherical support 31 by guide pulleys 42 and 48, and a tension pulley 44, and is driven in engagement with a drive pulley 46 having a plurality of teeth on its outer peripheral surface in which the teeth of the drive belt 40 engages the teeth of the drive pulley 46. The guide pulleys 42, 48 are rotatably mounted to a stationary base of the apparatus body 12. The tension pulley 44 is mounted on the stationary base thereof so as to be movable up and down, and is biased downward. The drive pulley 46 is rotated by an unshown drive motor which is mounted on the stationary base of the apparatus body 12.

The generally hemispherical support 31 is inclined or tilted in an arbitrary direction about the spot S with the movement of each of the two drive belts 40 which cross to each other perpendicularly. That is, as the drive pulley 46 is driven into rotation by the drive motor, the drive belt 40 starts moving and pulls downward the drive belt mounting arm 36 which is located on one side of the drive belt 40. With the movement of the drive belt 40, the generally hemispherical support 31 rotates or tilts about a horizontal axis that passes through the spot S (i.e. about an axis, passing the spot S, which is vertical relative to the drawing sheet in FIG. 4 or 5).

The tension pulley 44, which is biased downward, moves to a lower position 45 from the standard position 44 when the generally hemispherical support 31 is inclined, thus removing any flexure of the drive belts 40.

The drive motor is equipped with a pulse encoder so as to be able to calculate the inclination angle of the generally hemispherical support 31 due to the movement of the drive belts 40.

Next, a description is made below on how to perform a visual inspection of the photomask 80 by using this photomask surface inspection apparatus 10, with reference to FIGS. 6 to 9.

Figure 6:
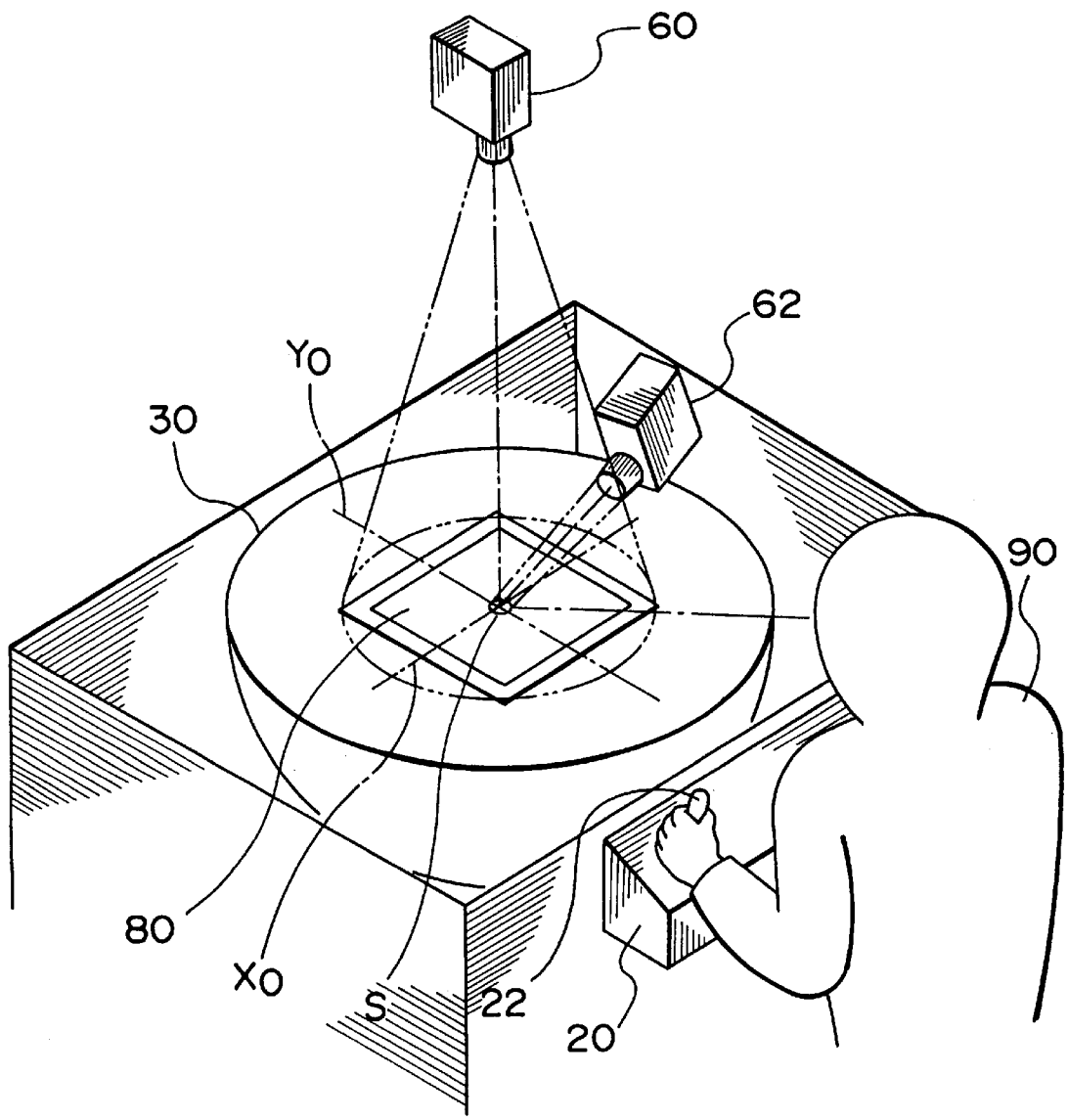
FIG. 6 is a schematic perspective view of the photomask surface inspection apparatus, shown in FIG. 1, which is ready for use.

FIG. 6 is a schematic perspective view showing a part of the photomask surface inspection apparatus which is ready for inspecting a photomask, and showing an inspector who handles the photomask surface inspection apparatus. The inspector 90 faces the inspection stage unit 30 through the unshown inspection window 16. In this state in which the photomask surface inspection apparatus is ready for inspecting the photomask, the photomask 80 is placed on and horizontally supported by the support plate 50 of the inspection stage unit 30. In this state, the support plate 50 is in the standard position in which the center of the support plate 50 is coincident with the spot S.

When the inspector performs a rough visual inspection of the photomask 80 as a whole, only the first illuminating lamp 60 which is just above the photomask 80 is used. On the other hand, when the inspector performs a precise visual inspection, a second illuminating lamp 62 which illuminates a small or minute region of the photomask 80 from a sideways direction with respect to the inspector 90 is used.

Figure 7:
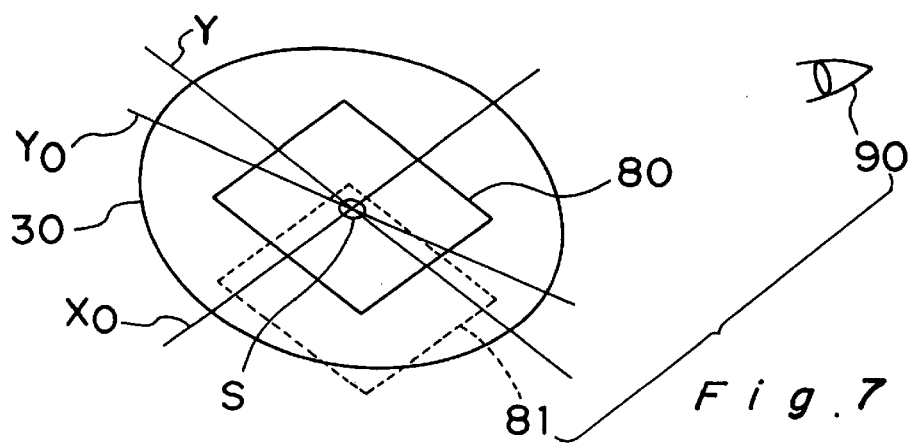
FIG. 7 is an explanatory view showing a process for inspecting a surface of the photomask.

For performing an elaborate visual inspection of the small region of the photomask 80 with small steps being carried out bit by bit, the support plate 50 is inclined or rotated about the $X_0$-axis as shown in FIG. 7 so that the support plate 50 is lowered at its forefront part and raised at its depth part with respect to the inspector 90.

Next, the table is moved in the X- and Y-directions, the photomask 80 is moved to a position shown by a reference numeral 81, and an upper right corner of the photomask 81 is lit up by the spotlight from the second illuminating lamp 62, as shown in FIG. 7.

Figure 8:
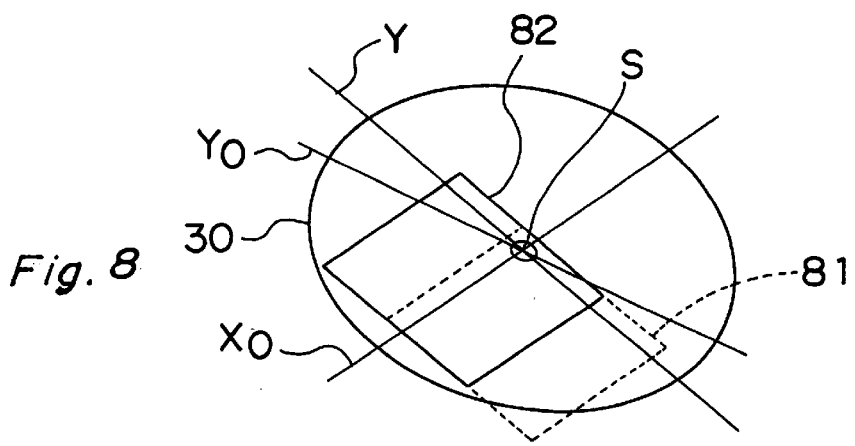
FIG. 8 is an explanatory view showing a process for inspecting the surface of the photomask.
Figure 9:
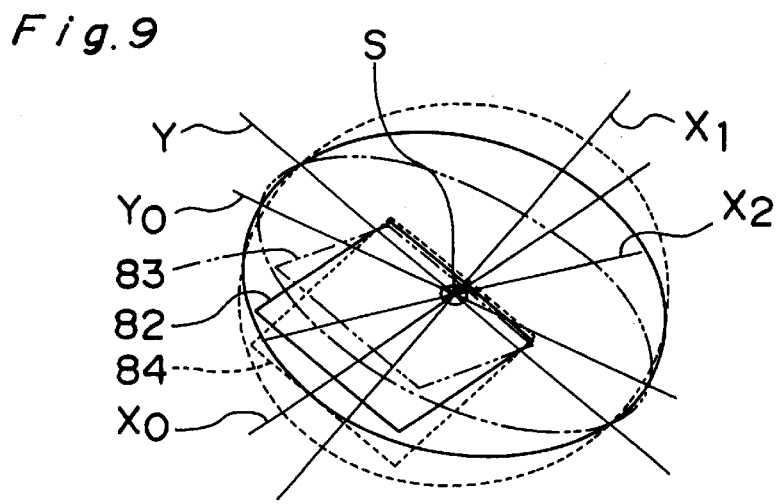
FIG. 9 is an explanatory view showing a process for inspecting the surface of the photomask.

Next, the support plate 50 is moved, in a direction of depth of the support plate 50, in the Y-direction so that the photomask 81 is moved to a position as shown by a reference numeral 82 in FIG. 8. When the spotlight from the second illuminating lamp 62 reaches the other corner of the photomask 80, the support plate 50 is moved a little bit rightward along the X-direction, and then the support plate 50 is moved forward to the inspector along the Y-direction.

Repeating the above steps to move the support plate 50, the whole surface of the photomask 80 is illuminated or lit by the spotlight sequentially.

By the way, this photomask surface inspection apparatus 10 allows a selection of a wave mode by which the whole inspection stage unit 30 is inclined periodically while the support plate 50 is moving, so that the photomask 80 moves as if its mask surface is undulating like a wave.

During the movement of the support plate 50, the inspector visually observes only the small region of the photomask 80 which is being illuminated with the spotlight. And, when the inspector discovers some abnormality on the small region thereof such as a partial brightness or shadow, the inspector presses a stop button of the operation unit 20 in order to stop the movement of the support plate 50.

Subsequently, if necessary, by operating the joy stick 22 of the operation unit 20 so that the support plate 50 tilts about the spot S, the inspector makes even more detailed inspection thereof. In case that a removable particle of dust etc. is deposited on the photomask 80, the inspector removes the particle of dust etc. by any suitable manner. Also, if the inspector decides that the photomask he/she inspects has some defect such as a particle of dust, a flaw, etc., the inspector can press an unshown defect memory button on the operation unit 20 in order to record its position of the defect of the photomask 80. Later, the inspector 90 can put back the photomask 80 onto the support plate 50, and then he/she can reinspect the corresponding part thereof of the photomask 80.

After the inspection of the whole surface of the photomask 80 is accomplished, the support plate 50 is returned to the standard position. Then, if necessary, the rotation unit 52 is operated so that the photomask 80 is changed in direction, for example, 90°, relative to its original direction. And with this state, the aforementioned steps to inspect the photomask 80 is again repeated. In this way, the photomask 80 is continuously inspected, for example, until it rotates 360°.

Further, if necessary, the photomask 80 is inverted by the transfer robot after the inspection of one side thereof is completed, and the inspector performs the visual inspection of the opposite side of the photomask 80.

After inspector finishes his/her visual inspection of the photomask 80, the photomask 80 is transferred from the support plate 50 into the storage case II on the second stage by the transfer robot.

With the use of this apparatus, a generation or raising of dust is prevented because the inspector is allowed to perform his/her visual inspection and to operate the apparatus from outside the apparatus, with the photomask 80 being isolated inside the apparatus where there is no person.

Also, because the inspector needs not hold the photomask 80 directly by his/her hand, his/her fatigue is effectively lightened or reduced.

Also, because the photomask 80 is automatically fed with respect to the spot S, the whole mask surface can be precisely inspected without an omission.

Also, because the spot S is stationary or unmovable, the inspector needs not move his/her eye or line of sight; therefore, he/she can concentrate his/her attention only on the region on which the spotlight impinges. Therefore, the working efficiency in the visual inspection is improved, and an improvement in precision of the inspection can also be expected.

Also, the photomask 80 can be automatically fed in such a manner that the mask surface thereof is changed in inclination periodically, i.e., that the mask surface thereof undulates like a wave. With the feeding of the photomask 80 in the manner described, any defect can be found more easily; thus, it is possible to realize an enhancement of precision in the inspection of the photomask 80.

Also, the spot S is stationary, and it does not move even if the mask surface of the photomask 80 is rotated or tilted. Therefore, when the inspector finds out a defect of the photomask 80 at the spot S and/or in its proximity, he/she can visually observe the defect thereof in more detail by rotating or tilting the mask surface of the photomask 80 so as to properly change an angle between the mask surface thereof and the spotlight, and an angle between the mask surface thereof and his/her line of sight, without loosing the view or sight of the defect.

Next, referring to FIGS. 10, 11 and 12, the description is made below on the photomask surface inspection apparatus 100 according to a second embodiment of the present invention.

First, the photomask surface inspection apparatus 100 is explained schematically.

Figure 10:
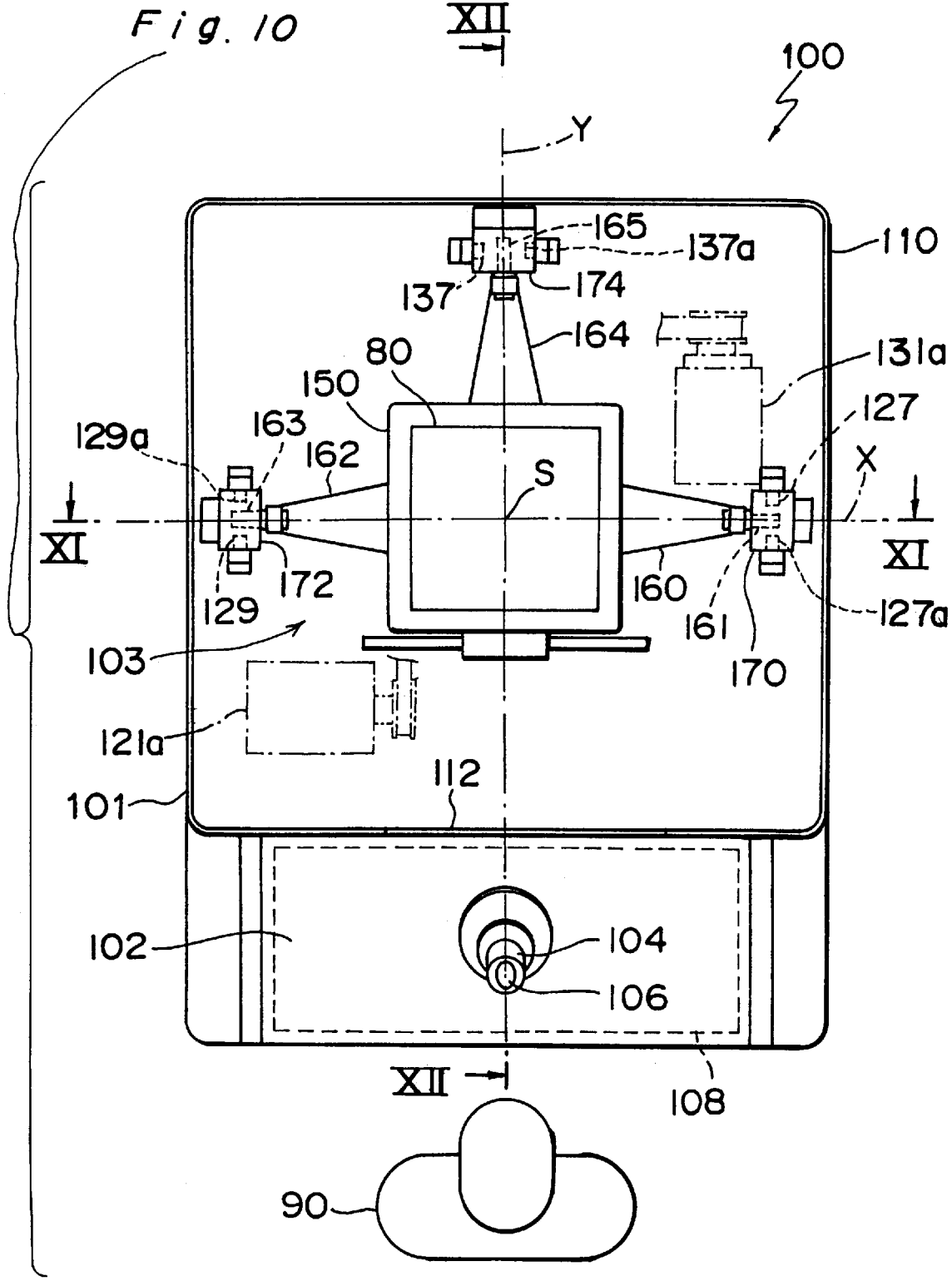
FIG. 10 is a plan view of a photomask surface inspection apparatus according to a second embodiment of the present invention.
Figure 11:
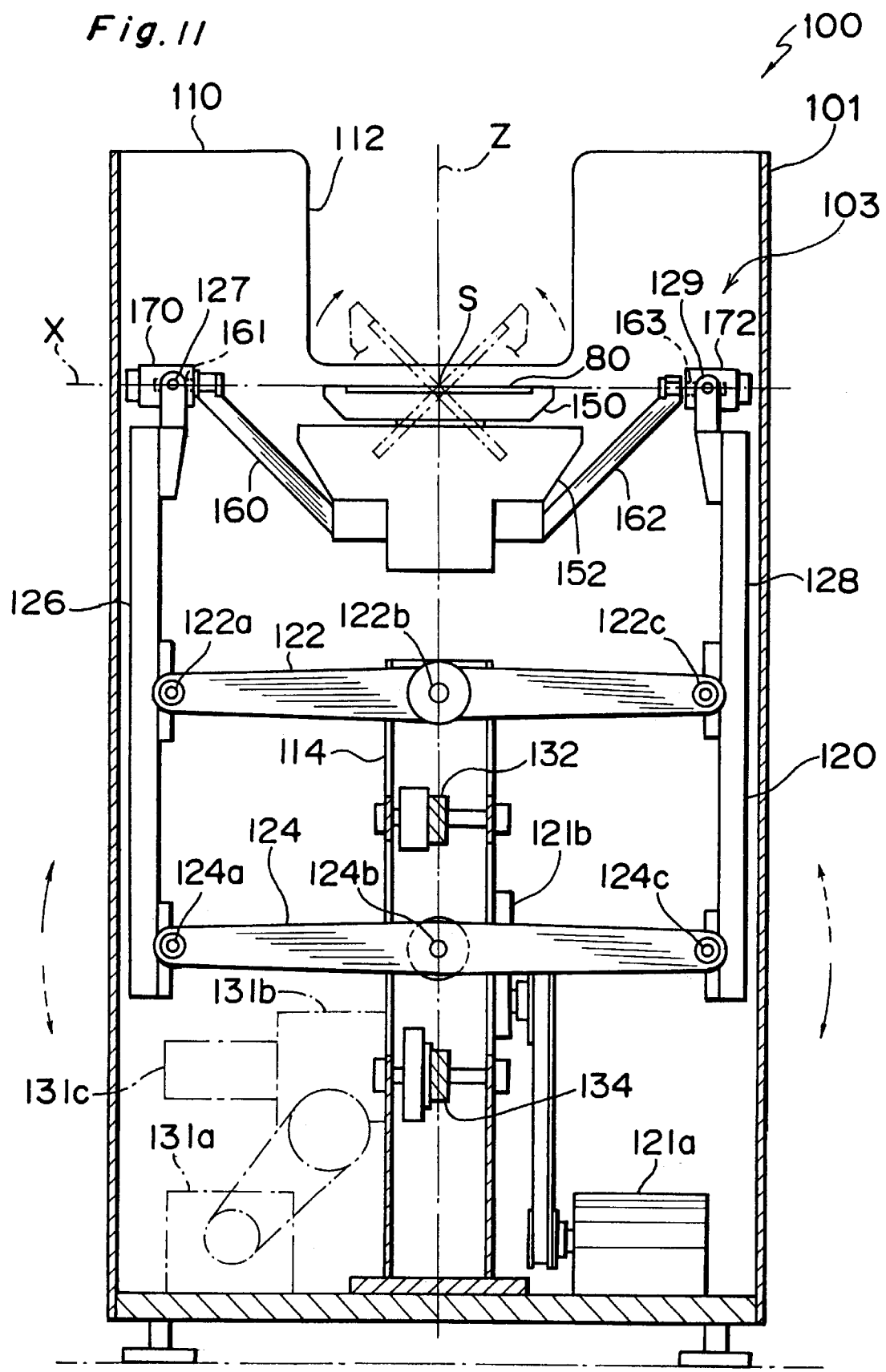
FIG. 11 is a sectional view taken generally along the line XI—XI of FIG. 10.
Figure 12:
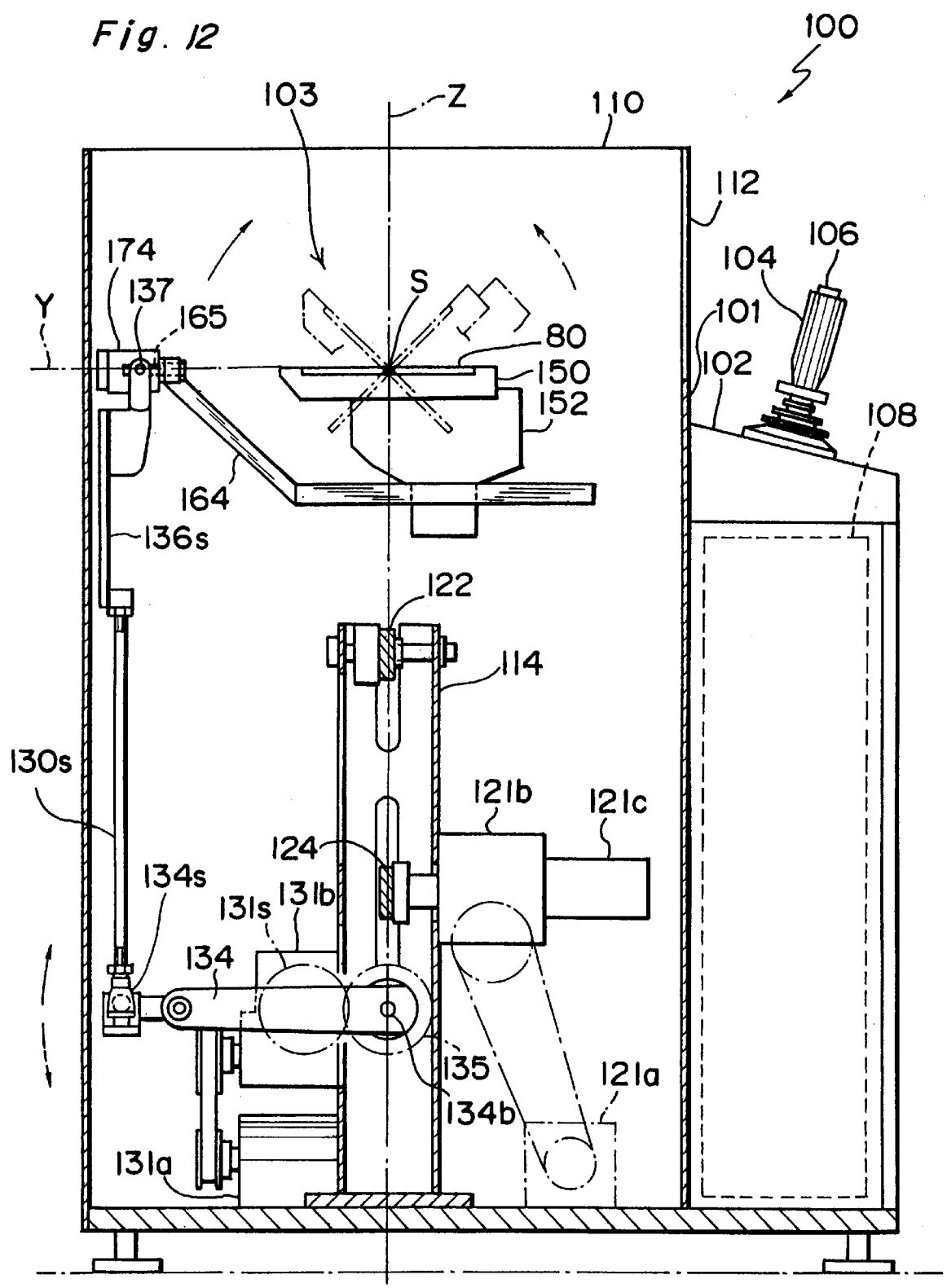
FIG. 12 is a sectional view taken generally along the line XII—XII of FIG. 10.

This photomask surface inspection apparatus 100 generally comprises a box-shaped apparatus body 101 and an operation unit 102 which is disposed in front of the apparatus body 101, as shown in FIG. 10 as a plan view of the photomask surface inspection apparatus 100, in FIG. 11 as a sectional view which is taken generally along the line XI—XI of FIG. 10, and in FIG. 12 as a sectional view which is taken generally along the line XII—XII of FIG. 10.

The apparatus body 101 is surrounded with a peripheral wall 110, and is opened at the top. Inside the apparatus body 101, there is installed an inspection stage unit 103 for positioning the photomask 80 thereon. A cutout 112 is formed in a fore portion of the peripheral wall 110. The inspector 90 can view the photomask 80 placed on the inspection stage unit 103 through the cutout 112. An operation unit 102 has a joy stick 104 provided on a top thereof and a control unit 108 accommodated inside the operation unit 102.

Next, a more detailed explanation is made on the inspection stage unit 103.

The inspection stage unit 103 generally comprises a support plate 150, an X-Y stage 152 (not shown in FIG. 10), support arms 160, 162, 164, a parallel link drive unit 120, and a link lifting device 130s (not shown in FIG. 10). The support plate 150 is supported at two points by the parallel link drive unit 120 and at one point by the link lifting device 130s. Namely, the support plate 150 is supported at three points in total.

As shown in the figures, one point on a horizontally extending surface being inspected of the photomask 80 which is placed on the support plate 150 in its standard position is a spot S, and mutually perpendicular three axes passing through the spot S are X-, Y- and Z-axes. That is, within a horizontal plane passing through the spot S, the X-axis extends right and left relative to the inspector 90, the Y-axis extends back and forth relative thereto, and the Z-axis extends vertical relative thereto.

A vicinity of the spot S is lit by an unshown illuminating device with an appropriate angle forming between the illuminating device and the surface being inspected of the photomask 80. The illuminating device may be provided either on the apparatus 100, or may be provided independently of the apparatus 100.

The support plate 150 has a recessed portion on its top surface for receiving the photomask 80 therein. The support plate 150 is supported by the X-Y stage 152. The X-Y stage 152 is supported by the support arms 160, 162, 164 which are coupled to one another in a generally T-shape, as shown in FIG. 10. That is, a pair of first support arms 160, 162 extend on both sides, respectively, along the X-axis, and the second support arm 164 extends backward along the Y-axis, where the support arms 160, 162, 164 are coupled to one another near the Z-axis.

The reason why the X-Y stage 152 is not supported at the front along the Y-axis is to downsize or miniaturize the apparatus and to provide a space for housing unshown cables connected to the X-Y stage 152.

Each of end portions of the support arms 160, 162, 164 is rotatably supported by each of upper end portions of longitudinal links 126, 128, 136s of the parallel link drive unit 120 and the link lifting device 130s via joint members (i.e. coupling members) 170, 172, 174, respectively.

More specifically, a pair of the first joint members 170, 172 are pivotally (i.e. rotatably) coupled both to the support pins 161, 163 which project outwardly in the X-direction from end portions of the support arms 160 and 162, respectively, and to each pair of support pins 127, 127a; 129, 129a in which the each pair 127, 127a; 129, 129a of the support pins project to each other along the Y-axis, respectively, from upper end portions (each of which is generally U-shaped in cross section perpendicular to the X-axis) of the respective longitudinal links 126, 128 of the parallel link drive unit 120.

The central axis of the support pin 161 of the first support arm 160, the central axis of the support pin 163 of the first support arm 162, and the spot S, are aligned so that they are on a straight line. This straight line crosses each of the central axes which connect each pair 127, 127a; 129, 129a of the support pins mounted on the respective upper end portions of the longitudinal links 126, 128.

On the other hand, the second joint member 174 is pivotally (i.e.rotatably) coupled both to a support pin 165 which projects outwardly in the Y-direction from an end portion of the second support arm 164, and to a pair of support pins 137, 137a which project to each other along the X-axis from an upper end portion (which is generally U-shaped in cross section perpendicular to the X-axis) of the longitudinal link 136s of the link lifting device 130s, respectively.

The parallel link drive unit 120 includes a parallel link mechanism which is arranged within a X-Z plane, as shown in FIG. 11.

More specifically, the parallel link drive unit 120 comprises a pair of lateral links 122, 124 each of which extends in the X-direction along the support plate 150 in which the pair of lateral links 122, 124 are parallel to each other, a pair of longitudinal links 126, 128 which are pivotally (i.e. rotatably) coupled to end portions 122a, 124a on one of the same sides of the lateral links 122, 124 and which are pivotally (i.e. rotatably) coupled to end portions 122c, 124c on the other of the same sides of the lateral links 122, 124 in which the pair of longitudinal links 126, 128 extend in the Z-direction so that they are parallel to each other, a drive motor 121a, and a speed reducer 121b.

Intermediate portions of the lateral links 122, 124 are pivotally (i.e. rotatably) supported by rotating shafts 122b and 124b which are mounted on a column 114, having a generally square cross section, being provided around the Z-axis. Each of these rotating shafts 122b, 124b crosses the Z-axis at one point and is parallel to the Y-axis. The longitudinal links 126, 128 are coupled to the lateral links 122, 124 so that the central axes of the support pins 127, 127a located at the upper end portion of one 126 of the longitudinal links, the end portion 122a of the lateral link 122 which rotatably connects to the longitudinal link 126, and the end portion 124a of the lateral link 124 which rotatably connects to the longitudinal link 126 are aligned on a straight line parallel to the Z axis as viewed from the direction of Y-axis, and so that the central axes of the support pins 129, 129a located at the upper end portion of the other 128 of the longitudinal links, the end portion 122c of the lateral link 122 which rotatably connects to the longitudinal link 128, and the end portion 124c of the lateral link 124 which rotatably connects to the longitudinal link 128 are aligned on a straight line parallel to the Z axis as viewed from the direction of Y-axis, as shown in FIG. 11.

The lower lateral link 124 is rotated by the drive motor 121a via the speed reducer 121b. The speed reducer 121b has a cam detector (i.e. a cam positioner) 121c (see FIG. 12) which is able to detect the angle of the lateral link 124.

On the other hand, the link lifting device 130s, as shown in FIG. 12, includes a link mechanism which is disposed within the Y-Z plane.

More specifically, the link lifting device 130s comprises a lateral link 134 which extends in the Y-direction parallel to and along the support plate 150, the longitudinal link 136s which extends generally in the Z axis, a drive motor 131a, and a speed reducer 131b. One end portion 134s of the lateral link 134 is coupled to the lower end part of the longitudinal link 136s by a ball joint, so that the longitudinal link 136s can tilt at any angle with respect to the lateral link 134.

The other end portion 134b of the lateral link 134 is pivotally (i.e. rotatably) supported by a rotating shaft which is provided on the column 114. This rotating shaft crosses the Z-axis perpendicularly at one point thereof and has a central axis which is parallel to the X-axis. The central axes of the support pins 137, 137a which are located at an upper end portion of the longitudinal link 136s, and the central axis of the coupling point at which the lower end portion of the longitudinal link 136s is coupled to the end portion 134s of the lateral link 134, are disposed on the same straight line which is parallel to the Z-axis.

The lateral link 134 is rotated or pivoted by the drive motor 131a via the speed reducer 131b. More specifically, an input gear 135 which is fixed to an end portion 134b of the lateral link 134 engages an output gear 131s of the speed reducer 131b, in which the speed reducer 131b does not interfere with the lateral link 124 of the parallel link drive unit 120. A cam detector (i.e. a cam positioner) 131c (see FIG. 11) is provided on the speed reducer 131b which can detect the angle of the lateral link 134.

Next, a description is made below on how the parallel link drive unit 120 and the link lifting device 130s operate, respectively.

First, the description is made on the parallel link drive unit 120.

When the drive motor 121a is rotated, the lower lateral link 124 is pivoted (i.e. rotated), as shown by an arrow in FIG. 11, so that one of the longitudinal links 126, 128 goes up and the other thereof goes down. Accompanying this movement of the longitudinal links 126, 128, one of the joint members 170, 172 goes up and the other thereof goes down. The opposed lateral links 122, 124 are coupled so as to be parallel to each other, and the opposed longitudinal links 126, 128 are coupled so as to be parallel to each other. Therefore, the support plate 150 is pivoted about the Y-axis passing through the spot S, as shown by a one-dot chain line in FIG. 11.

Next, the description is made on the link lifting device 130s.

When the drive motor 131a is rotated, the lateral link 134 is pivoted or rotated, as shown by an arrow in FIG. 12, so that the longitudinal link 136s goes up and down. As a result, the second joint member 174 also goes up and down, and the support plate 150 is pivoted or rotated about a line connecting the central axes of the support pins 161, 163 of the first support arms 160, 162 and the spot S to each other.

More specifically, the second joint member 174 moves within a plane which is perpendicular to a straight line connecting the central axes of the support pins 161, 163 of the first support arms 160, 162 and the spot S, and which passes through the spot S.

However, the straight line connecting the central axes of the support pins 161, 163 of the first support arms 160, 162 and the spot S is inclined relative to the horizontal line of the X-axis by the parallel link drive unit 120. Therefore, the second joint member 174 is moved along a spherical surface defined by the X-, Y- and Z-axes around the spot S. In other words, when the straight line connecting the central axes of the support pins 161, 163 of the first support arms 160, 162 and the spot S is horizontal, the longitudinal link 136s goes up and down in a vertical direction parallel to the Z-axis within the X-Z plane; meanwhile, when the straight line connecting the central axes of the support pins 161, 163 of the first support arms 160, 162 and the spot S is tilted from the horizontal, the longitudinal link 136s goes up and down with a state in which the longitudinal link 136s is inclined (i.e. not parallel to the Z-axis) about the end portion 134s, constructed as the ball joint, of the lateral link 134.

Consequently, the support plate 150, with its top surface being directed upward, can be tilted in every direction about the spot S, based on the combination of the pivoting or rotation by the parallel link drive unit 120, and the pivoting or rotation by the link lifting device 130s. That is, the photomask 80 can be inclined without moving one point (namely, the spot S) on the surface, to be inspected, of the photomask 80.

Next, an explanation is made below on how this apparatus 100 is used and operated.

First, the photomask 80 is placed on the support plate 150, and then an unshown illuminating device lights up a part of the photomask 80 which corresponds to a vicinity of the spot S.

Then, the inspector observes the illuminated region of the photomask 80 while he/she sequentially moves the photomask 80 relative to the illuminating region by operating the joy sticks 104. At this step, when the joy stick 104 is tilted with a button 106, provided at the upper end of the joy stick 104, being pressed downward, the X-Y stage 152 is driven corresponding to the tilting direction so that the support plate 150 is translated along the surface to be inspected of the photomask 80 in the direction in which the joy stick 104 is tilted. Releasing the button 106 or returning the joy stick 104 to its neutral position causes the support plate 150 to be stopped. On the other hand, tilting the joy stick 104 with the button 106 being released, causes the parallel link drive unit 120 and/or the link lifting device 130s to be driven in correspondence to the tilting direction, so that the support plate 150 is inclined in the direction in which the joy stick 104 is tilted.

The translating speed or inclining speed of the support plate 150 at time of operating the joy stick 104 can be set freely beforehand, by a volume control dial which is provided on the control unit 108.

Alternatively, the photomask surface inspection apparatus may be so constructed that pressing an unshown automatic operation button causes the parallel link drive unit 120 and/or the link lifting device 130s to be actuated to swing the support plate 150, as required, in a pre-programmed specified pattern and causes the X-Y stage 152 to be automatically actuated to move the support plate 150, as required, with respect to the spot S. In this arrangement, the photomask surface inspection apparatus may be so constructed that pressing an unshown stop switch, upon finding any abnormality, realizes a changeover in mode from the automatic operation to the manual operation.

The photomask surface inspection apparatus 100 according to the second embodiment, constructed as described above, realizes not only an improvement of the working efficiency in visual inspection of the photomask 80 and an improvement of precision in the inspection thereof, like the photomask surface inspection apparatus 10 of the first embodiment, but also an easy miniaturization (i.e. downsize) of the apparatus and a facilitation of control in the inclination of the support plate 150.

That is, in the photomask surface inspection apparatus 10 of the first embodiment, the drive belt mounting arms 36 need to be protrusively provided outside and above the generally hemispherical support 31 so that the drive belts 40 do not interfere with the generally hemispherical member 31 when the generally hemispherical member 31 is inclined. In this apparatus 100, however, the joint members 170, 172, 174 can be disposed in proximity to one another on the generally same surface as the support plate 150. Therefore, the apparatus is easy to be miniaturized.

Further, in the photomask surface inspection apparatus 10 of the first embodiment, it is necessary to place the drive belts 40 at 45° with respect to the inspector, and it is necessary to drive both of the drive belts 40 in response to the longitudinal or lateral operation of the joy stick 22. In this apparatus 100 of the second embodiment, however, it is possible to drive either the parallel link drive unit 120 or the link lifting device 130s in response to a longitudinal or lateral operation of the joy stick 104. Therefore, the support plate 150 becomes easier to control for its inclination.

Next, referring to FIGS. 13 and 14, a description is made below on the photomask surface inspection apparatus 100X according to a third embodiment of the present invention.

The photomask surface inspection apparatus 100x of the third embodiment is generally similar in construction to the photomask surface inspection apparatus 100 of the second embodiment, but the photomask surface inspection apparatus 100x of the third embodiment differs from that of the second embodiment in that the ball joint is used not for the link lifting device but for the parallel link drive unit. Hereinbelow, like or corresponding component members or parts are designated by like reference numerals, and the description is made below mainly on different points therebetween.

Figure 13:
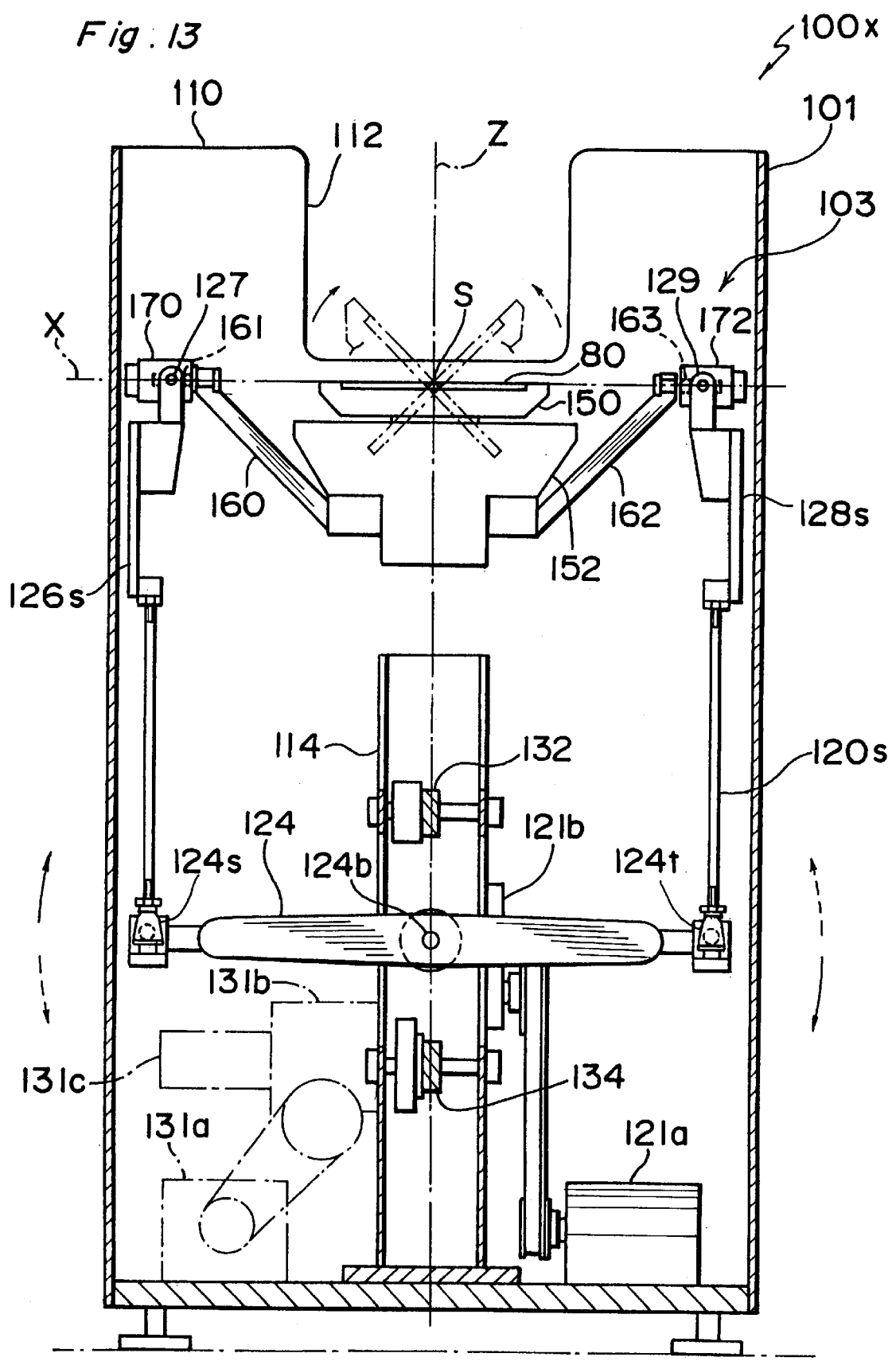
FIG. 13 is a sectional view of a photomask surface inspection apparatus according to a third embodiment of the present invention.

A parallel link drive unit 120s includes a link mechanism which is disposed within the X-Z plane as shown in FIG. 13, corresponding to FIG. 11. That is, the parallel link drive unit 120s comprises a lateral link 124 extending in the X-direction which is parallel to and along the support plate 150, a pair of longitudinal links 126s, 128s which are coupled to end portions 124s, 124t of the lateral link 124 by ball joints so as to be rotatable in every direction and which extend generally parallel to each other in the direction of the Z-axis, a drive motor 121a, and a speed reducer 121b.

An intermediate portion of the lateral link 124 is rotatably supported by a rotating shaft (i.e. a rotating axis) 124b which is provided on a column 114 having a generally rectangular cross section and protrusively provided around the Z-axis. This rotating shaft perpendicularly crosses the Z-axis at one point on the Z-axis and has a central axis which is parallel to the Y-axis.

The longitudinal links 126s, 128s are rotatably coupled to both end portions 124s, 124t of the lateral link 124 via the ball joints, respectively. The lateral link 124 is rotated or pivoted by the drive motor 121a via the speed reducer 121b, and its angle is detected by a cam detector (i.e. a cam position) 121c (see FIG. 14).

Figure 14:
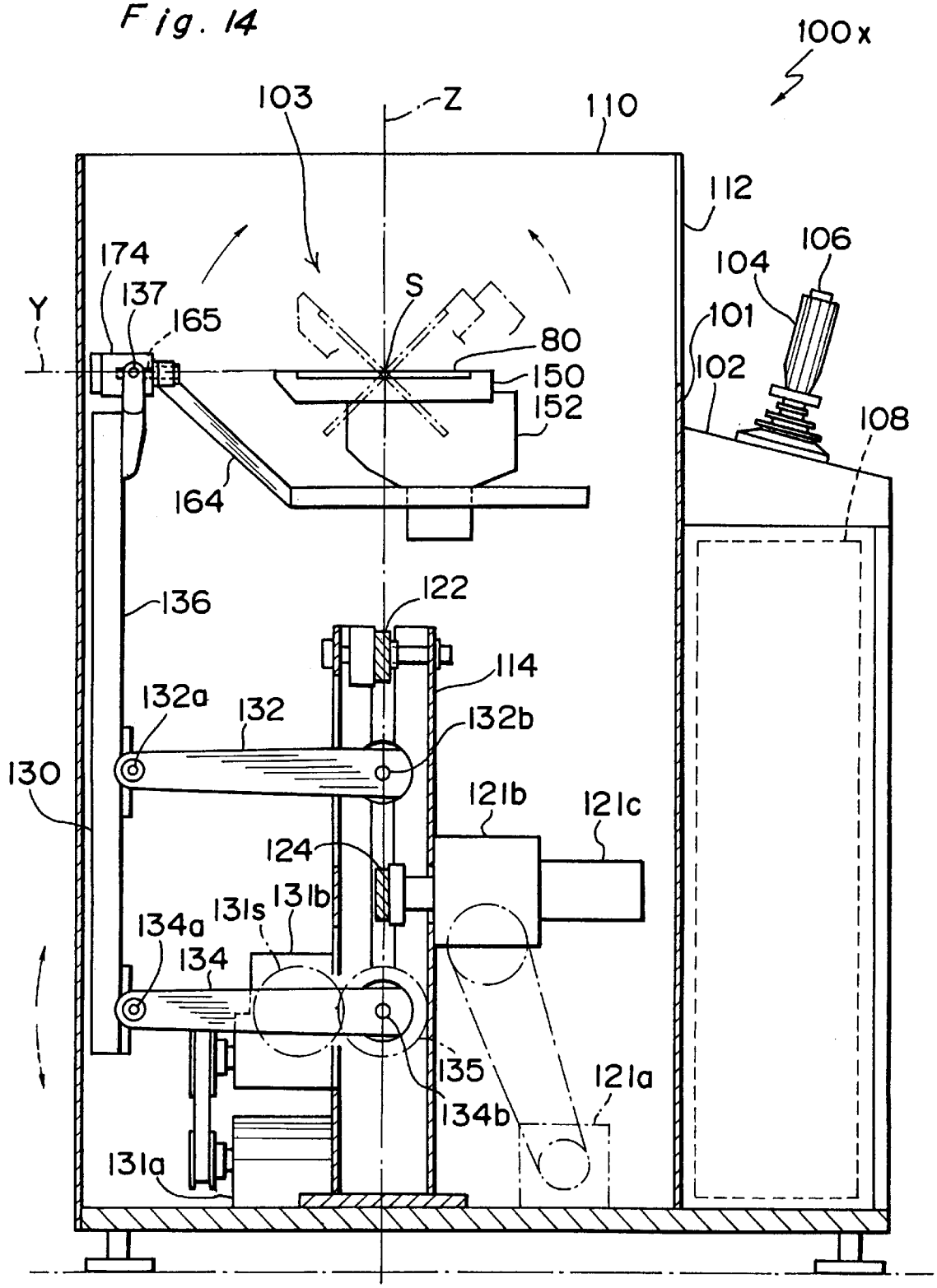
FIG. 14 is a sectional view of the photomask surface inspection apparatus according to the third embodiment of the present invention.

The link lifting device 130, as shown in FIG. 14, includes a parallel link mechanism which is disposed within the Y-Z plane. That is, the link lifting device 130 comprises a pair of lateral links 132, 134 extending along the support plate 150 in the Y-direction and extending parallel to each other, a longitudinal link 136, extending in the Z-direction, to which end portions 132a, 134a on the same side of the lateral links 132, 134 are rotatably connected, a drive motor 131a, and a speed reducer 131b. The other end portions on the same side of the lateral links 132, 134 are pivotally supported by rotating shafts 132b, 134b which are mounted on the column 114. Each of these rotating shafts 132b, 134b crosses the Z-axis at one point on the Z-axis so that it is perpendicular to the Z-axis and it has a central axis parallel to the X-axis.

The longitudinal link 136 is rotatably coupled to both the lateral links 132, 134 so that a central axis of a support pin 137 being provided at an upper end portion of the longitudinal link 136, and the central axes of the shafts 132a, 134a as the coupling points at which the longitudinal link 136 is rotatably coupled to the end portions of the lateral links 132, 134, are aligned on a straight line, as viewed in the X-direction, and so that this straight line is parallel to the Z-axis. The lower lateral link 134 is rotated by the drive motor 131a via the speed reducer 131b.

Next, an explanation is made below on how the parallel link drive unit 120s and the link lifting device 130 are operated, respectively.

In the link lifting device 130, when the drive motor 131a is rotated, the lower lateral link 134 of the lifting device 130 is driven and rotated, as shown by an arrow in FIG. 14. As a result, the longitudinal link 136 goes up and down. Accompanying this movement of the longitudinal link 136, the second joint member 174 is lifted and lowered, and the support plate 150 is rotated about a line which connects the central axes of the support pins 161, 163 of the support pins 160, 162, and the spot S.

Meanwhile, in the parallel link drive unit 120s, when the drive motor 121a is rotated, the lateral link 124 of the parallel link drive unit 120s is rotated, as shown by an arrow in FIG. 13, so that one of the longitudinal links 126s, 128s goes up and the other thereof goes down. As a result, one of the first joint members 170, 172 goes up and the other thereof goes down. The first joint members 170, 172 are rotated within a plane perpendicular to a line which passes both the spot S and a center of the support pin 165 of the second support arm 164.

When the parallel link drive unit 120s is actuated with the line which connects both the spot S and the center of the support pin 165 of the second support arm 164 being inclined relative to the horizontal (i.e. relative to the Y-axis), the joint members 170, 172 are moved in the X-, Y- and Z-directions within a plane which is perpendicular to a straight line connecting both the spot S and the support pin 165 of the second support arm 164 and which passes the spot S. Therefore, the longitudinal links 126s, 128s are inclined about the end portions 124s, 124t of the lateral link 124, respectively. However, the support plate 150 is coupled to the longitudinal link 136 of the link lifting device 130 so as to be permitted to rotate only within the X-Z plane., and the up-and-down absolute amount in movement along the Z-axis of one of the first joint members 170, 172 is equal to that of the other thereof; therefore, the spot S is not moved.

Namely, the combination in movement of the rotation by the parallel link drive unit 120s and of the rotation by the link lifting device 130, allow the support plate 150 to be able to tilt in any direction about the spot S.

It is to be noted that the present invention is not limited to the aforementioned three embodiments, and can be embodied in other various ways.

For example, in the apparatuses 100, 100x of the second and third embodiments, the parallel link drive units 120, 120s and the link lifting devices 130, 130s may be driven in other proper ways. For example, the longitudinal links 126, 126s, 136, 136s may be lifted and lowered by a cylinder.

Alternatively, in the second embodiment, the support plate 150 may be rotated about the line connecting the central axes of the support pins 161, 163 and the spot S by a driving unit other than the link lifting device 130s.

Alternatively, in the second embodiment, the lateral links 122, 124 of the parallel link drive unit 120 may be reduced in length, for example, to a half, and the longitudinal links 126, 128 may be formed L-shaped.

Alternatively, in the second embodiment, instead of using the link lifting device 130s, a second parallel link drive unit which is constructed similar to the parallel link drive unit 120s of the third embodiment may be disposed perpendicular to the parallel link drive unit 120, where the support plate 150 is supported by four points, not by three points.

Alternatively, the aforementioned apparatuses 10, 100, 100x of the above embodiments may be used for inspecting a surface other than the surface of the photomask,. for example, a surface of a wafer.

Further, the inspection is not limited to the inspection by the eye(s) of the inspector. For example, it is possible to automatically inspect the surface of the photomask, etc. by a camera, etc.

Although the present invention has been fully described in connection with the preferred embodiments thereof with reference to the accompanying drawings, it is to be noted that other various changes and modifications are apparent to those skilled in the art. Such changes and modifications are to be understood as included within the scope of the present invention as defined by the appended claims unless they depart therefrom.

What is claimed is:

1. A surface inspection apparatus comprising:
   a support plate on which a planar object to be inspected is put;
   a lighting device which lights a point and a vicinity of the point of a surface to be inspected of the planar object that is put on the support plate;
   a first driving device which is supported by a stationary base, and which tilts the support plate about a tilting point corresponding to the point of the surface lit up by the lighting device so that a normal line to the surface, passing the tilting point, of the planar object tilts in every direction;
   a second driving device which moves the support plate in two directions, generally perpendicular to each other, along the surface of the planar object which is put on the support plate;
   a bowl-like support generally hemispherical in shape that has a peripheral surface corresponding to a part of a sphere with a center point corresponding to the point lit up, by the lighting device, of the planar object, wherein the support plate is provided inside the bowl-like support, in which the planar object is supported on the support plate so that the planar object is positioned at a level which is generally equal to a level of a periphery of the bowl-like support, wherein the second driving device is provided inside the bowl-like support, and wherein the first driving device moves the bowl-like support along the sphere.

2. The surface inspection apparatus as claimed in claim 1, which further comprises a third driving device which rotates the support plate about a rotation axis which is parallel to the normal line to the surface of the planar object which is put on the support plate.

3. A surface inspection apparatus comprising:

a support plate on which a planar object to be inspected is put;

a lighting device which lights a point and a vicinity of the point of a surface to be inspected of the planar object that is put on the support plate;

a first driving device which is supported by a stationary base, and which tilts the support plate about a tilting point corresponding to the point of the surface lit up by the lighting device so that a normal line to the surface, passing through the tilting point, of the planar object tilts in every direction, the first driving device including:

at least three longitudinal links which are provided around a standard axis that passes through the tilting point and that is generally perpendicular to the surface of the planar object, and which are provided generally parallel to the standard axis, in which each of the at least three longitudinal links is connected to one of the support plate and a plate support member that supports the support plate; and a rising and falling device for making the longitudinal links rise and fall parallel to the standard axis, wherein at least one of the longitudinal links, and structures parallel to the standard axis form a first link pair, wherein there is provided a second link pair which is provided parallel to the surface of the planar object, in which the first link pair and the second link pair form a parallel link mechanism, wherein the at least one of the longitudinal links, and one of the support plate and the plane support member, are prevented from rotating relative to each other about an axis which corresponds to a direction in which the at least one of the longitudinal links extends, and a second driving device which moves the support plate in two directions, generally perpendicular to each other, along the surface of the planar object which is put on the support plate.

4. A surface inspection apparatus comprising:

a support plate on which a planar object to be inspected is put;

a lighting device which lights a point and a vicinity of the point of a surface to be inspected of the planar object that is put on the support plate;

a first driving device which is supported by a stationary base, and which tilts the support plate about a tilting point corresponding to the point of the surface lit up by the lighting device so that a normal line to the surface, passing the tilting point, of the planar object tilts in every direction, the first driving device including a parallel link drive mechanism and a link ascending and descending mechanism, wherein the parallel link drive mechanism comprises:

a pair of first lateral links which are provided parallel to the surface of the planar object within a standard plane which includes a standard axis that passes through the tilting point and is generally perpendicular to the surface of the planar object, in which a middle part of each of the pair of first lateral links is rotatably mounted to the stationary base via a rotation axis that passes through the standard axis and is perpendicular to the standard plane; and a pair of first longitudinal links which are provided on both sides of the standard axis within the standard plane so as to be parallel to the standard axis, in which the pair of first longitudinal links are rotatably connected to both ends of each of the pair of first lateral links, and in which the pair of first longitudinal links are rotatably connected to one of the support plate and a plate support member that supports the support plate, through at least a first joint, within the standard plane, wherein the link ascending and descending mechanism comprises:

a second lateral link which is provided parallel to the surface of the planar object within a plane that passes through the standard axis and is perpendicular to the standard plane, in which one of ends of the second lateral link is mounted on the stationary base rotatably about a rotation axis which is perpendicular to the standard axis within the standard plane;

a second longitudinal link which is provided generally parallel to the standard axis in a region including the plane that passes through the standard axis and is perpendicular to the standard plane, in which one of ends of the second longitudinal link is rotatably connected to the other of ends of the second lateral link through a second joint, and in which the other of ends of the second longitudinal link is rotatably connected to one of the support plate and the plate support member through a third joint, and a second driving device which moves the support plate in two directions, generally perpendicular to each other, along the surface of the planar object which is put on the support plate.

5. The surface inspection apparatus as claimed in claim 4, wherein the first joint comprises a joint body in which the one of the support plate and the plate support member can rotate relative to the joint body about a first axis that is perpendicular to the standard axis and that is parallel to the standard plane, and in which the first longitudinal link can rotate relative to the joint body about a second axis that is perpendicular both to the standard axis and to the standard plane, wherein the second joint is a universal joint, and wherein the third joint comprises a joint body in which the one of the support plate and the plate support member can rotate relative to the joint body of the third joint about the second axis that is perpendicular both to the standard axis and to the standard plane, and in which the second longitudinal link can rotate relative to the joint body of the third joint about the first axis that is parallel to the standard plane and that is perpendicular to the standard axis.

6. The surface inspection apparatus as claimed in claim 5, wherein the first joint comprises:

a pin which extends from an end of the one of the support plate and the plate support member in which the pin extends in a direction of the first axis that is perpendicular to the standard axis and that is parallel to the standard plane;

a hole which forms on the joint body of the first joint in which the pin of the first joint rotatably engages the hole;

a pin which extends from an end of the first longitudinal link in which the pin extends in the direction of the second axis that is perpendicular both to the standard plane and to the standard axis; and a hole which forms on the joint body of the first joint in which the pin of the first longitudinal link rotatably engages the hole, wherein the universal joint is a ball joint, and wherein the third joint comprises:
 a pin which extends from an end of the one of the support plate and the plate support member in which the pin extends in a direction of the second axis that is perpendicular both to the standard axis and to the standard plane;
 a hole which forms on the joint body of the third joint in which the pin of the one of the support plate and the plate support member rotatably engages the hole of the third joint;
 a pin which extends from an end of the second longitudinal link in which the pin extends in the direction of the first axis that is parallel to the standard plane and that is perpendicular to the standard axis; and
 a hole which forms on the joint body of the third joint in which the pin of the second longitudinal link rotatably engages the hole.

7. A surface inspection apparatus comprising:

a support plate on which a planar object to be inspected is put;

a lighting device which lights a point and a vicinity of the point of a surface to be inspected of the planar object that is put on the support plate;

a first driving device which is supported by a stationary base, and which tilts the support plate about a tilting point corresponding to the point of the surface lit up by the lighting device so that a normal line to the surface, passing the tilting point, of the planar object tilts in every direction, the first driving device including a parallel link drive mechanism and a link ascending and descending mechanism, wherein the parallel link drive mechanism comprises:
 a first lateral link which is provided parallel to the surface of the planar object within a standard plane which includes a standard axis that passes through the tilting point and that is generally perpendicular to the surface of the planar object, in which a middle part of the first lateral link is rotatably mounted to the stationary base via a rotation axis that passes through the standard axis and is perpendicular to the standard plane; and
 a pair of first longitudinal links which are provided generally parallel to the standard axis in a region including the standard plane and which are provided on both sides of the standard axis, in which one of ends of each first longitudinal link is rotatably connected to each end of the first lateral link through a first joint, and in which the other of ends of each first longitudinal link is rotatably connected to one of the support plate and a plate support member which supports the support plate, through a second joint, wherein the link ascending and descending mechanism comprises:
 a pair of second lateral links which are provided parallel to the surface of the planar object within a plane which passes through the standard axis and is perpendicular to the standard plane, in which one of ends of each second lateral link is rotatably supported by the stationary base through a rotation axis that is perpendicular to the standard axis and that is parallel to the standard plane, and in which the other of ends of one of the second lateral links and the other of ends of the other of the second lateral links are on a same side relative to the standard axis; and
 a second longitudinal link which are provided parallel to the standard axis within the plane which passes through the standard axis and is perpendicular to the standard plane, in which the second longitudinal link is rotatably connected to the others of ends of the second lateral links through a pair of axes that are perpendicular to the standard axis and that are parallel to the standard plane, and in which the second longitudinal link is rotatably connected to one of the support plate and the plate support member through a third joint within the plane that is perpendicular to the standard plane with a state in which the second longitudinal link and the one of the support plate and the plate support member are prevented from rotating relative to each other about an axis which corresponds to a direction in which the second longitudinal link extends, and
 a second driving device which moves the support plate in two directions, generally perpendicular to each other, along the surface of the planar object which is put on the support plate.

8. The surface inspection apparatus as claimed in claim 7, wherein the first joint is a universal joint, wherein the second joint comprises a joint body in which the one of the support plate and the plate support member can rotate relative to the joint body about a first axis that is perpendicular to the standard axis and that is parallel to the standard plane, and in which the first longitudinal link can rotate relative to the joint body about a second axis that is perpendicular both to the standard axis and to the standard plane, and wherein the third joint comprises a joint body in which the one of the support plate and the plate support member can rotate relative to the joint body of the third joint about the second axis that is perpendicular both to the standard axis and to the standard plate, and in which the second longitudinal link can rotate relative to the joint body of the third joint and the first axis that is perpendicular to the standard axis and that is parallel to the standard plane.

9. The surface inspection apparatus as claimed in claim 8, wherein the universal joint is a ball joint, wherein the second joint comprises:
 a pin which extends from an end of the one of the support plate and the plate support member in which the pin extends in a direction of the first axis that is perpendicular to the standard axis and that is parallel to the standard plane;
 a hole which forms on the joint body of the second joint in which the pin of the second joint rotatably engages the hole;
 a pin which extends from an end of the first longitudinal link in which the pin extends in the direction of the second axis that is perpendicular both to the standard plane and to the standard axis; and a hole which forms on the joint body of the second joint in which the pin of the first longitudinal link rotatably engages the hole, and wherein the third joint comprises:

a pin which extends from an end of the one of the support plate and the plate support member in which the pin extends in a direction of the second axis that is perpendicular both to the standard axis and to the standard plane;

a hole which forms on the joint body of the third joint in which the pin of the one of the support plate and the plate support member rotatably engages the hole of the third joint;

a pin which extends from an end of the second longitudinal link in which the pin extends in the direction of the first axis that is parallel to the standard plane and that is perpendicular to the standard axis; and a hole which forms on the joint body of the third joint in which the pin of the second longitudinal link rotatably engages the hole.

* * * * *